US009969777B2

(12) United States Patent
Britton et al.

(10) Patent No.: US 9,969,777 B2
(45) Date of Patent: May 15, 2018

(54) MUTANT SPIKE PROTEIN EXTENDING THE TISSUE TROPISM OF INFECTIOUS BRONCHITIS VIRUS (IBV)

(71) Applicant: THE PIRBRIGHT INSTITUTE, Woking, Surrey (GB)

(72) Inventors: Paul Britton, Woking (GB); Erica Bickerton, Woking (GB)

(73) Assignee: THE PIRBRIGHT INSTITUTE, Woking, Surrey (GB)

( * ) Notice: Subject to any disclaimer, the term of this patent is extended or adjusted under 35 U.S.C. 154(b) by 0 days. days.

(21) Appl. No.: 14/888,388

(22) PCT Filed: May 1, 2014

(86) PCT No.: PCT/GB2014/051353
§ 371 (c)(1),
(2) Date: Oct. 30, 2015

(87) PCT Pub. No.: WO2014/177873
PCT Pub. Date: Nov. 6, 2014

(65) Prior Publication Data
US 2016/0060303 A1    Mar. 3, 2016

(30) Foreign Application Priority Data
May 3, 2013    (GB) .................................. 1308057.7

(51) Int. Cl.
| C07K 14/165 | (2006.01) |
| A61K 39/215 | (2006.01) |
| C07K 14/005 | (2006.01) |
| C12N 7/00 | (2006.01) |
| A61K 39/12 | (2006.01) |
| A61K 39/00 | (2006.01) |

(52) U.S. Cl.
CPC ............ *C07K 14/005* (2013.01); *A61K 39/12* (2013.01); *A61K 39/215* (2013.01); *C12N 7/00* (2013.01); *A61K 39/00* (2013.01); *C07K 14/165* (2013.01); *C12N 2770/20021* (2013.01); *C12N 2770/20022* (2013.01); *C12N 2770/20034* (2013.01); *C12N 2770/20052* (2013.01)

(58) Field of Classification Search
None
See application file for complete search history.

(56) References Cited

U.S. PATENT DOCUMENTS 3,876,763 A * 4/1975 Iritani ..................... A61K 39/17
424/201.1

FOREIGN PATENT DOCUMENTS

| WO | WO-2004/078203 A2 | 9/2004 |
| WO | WO-2011/004146 A1 | 1/2011 |

OTHER PUBLICATIONS

Binns et al. Cloning and Sequencing of the Gene Encoding the Spike Protein of the Coronavirus IBV. J. Gen. Virol., 1985 66: 719-726.*
GenBank: CAA26201.1. unnamed protein product [Infectious bronchitis virus]. Dated Jul. 26, 1995.*
Yamada et al. Acquisition of Cell-Cell Fusion Activity by Amino Acid Substitutions in Spike Protein Determines the Infectivity of a Coronavirus in Cultured Cells. PLoS One. 2009. 4:e6130.*
GenBank: AAY24433.1. spike protein [Infectious bronchitis virus]. Oct. 17, 2005.*
GenBank: DQ830981.1. Infectious bronchitis virus isolate Beaudette 42 spike glycoprotein gene, complete cds. Jun. 14, 2007.*
GenBank: AAY21247.1. Spike protein [Infectious bronchitis virus], dated May 2, 2005.*
GenBank: AAY21245.1. spike protein [Infectious bronchitis virus]. dated May 2, 2005.*
Tay et al. 2012. Characterization of cellular furin content as a potential factor determining the susceptibility of cultured human and animal cells to coronavirus infectious bronchitis. Virology. 433(2):421-30. Epub Sep. 18, 2012. (Year: 2012).*
Armesto et al., Transient dominant selection for the modification and generation of recombinant infectious bronchitis coronaviruses, *Meth. Molec. Biol.*, 454:255-73 (2008).
Atschul et al., Basic Local Alignment Search Tool, *J. Mol. Biol.*, 403-10 (1990).
Ausubel et al., Current protocols in Molecular Biology, Chapter 18 (1999).
Bickerton, Cellular tropism and cell-to-cell fusion properties of the infectious bronchitis virus spike glycoprotein, *Univ. Warwick*, (2010).
Britton et al., Generation of a recombinant avian coronavirus infectious bronchitis virus using transient dominant selection, *J. Virol. Meth.*, 123:203-11 (2005).
Casais et al., Recombinant avian infectious bronchitis virus expressing a heterologous spike gene demonstrates that the spike protein is a determinant of cell tropism, *J. Virol.*, 77:9084-9 (2003).
Casais et al., Reverse genetics system for the avian coronavirus infectious bronchitis virus, *J. Virol.*, 75:12359-69 (2001).
Devereux et al., A comprehensive set of sequence analysis programs for the VAX, *Nuc. Acids Res.*, 12:387 (1984).
Li et al., Sequence analysis of nephropathogenic infectous bronchitis virus strains of the Massachusetts genotype in Beijing, *Avian Patholog.*,30(5):535-41 (2001).

(Continued)

*Primary Examiner* — Nianxiang Zou
(74) *Attorney, Agent, or Firm* — Marshall, Gerstein & Borun LLP

(57) ABSTRACT

The present invention provides an infectious bronchitis virus (IBV) spike protein (S protein) which is based on an S protein from an IBV strain with restricted tissue tropism, but which comprises the sequence XBBXBX in the part of the S2 protein corresponding to residues 686 to 691 of the sequence given as SEQ ID No. 2, where B is a basic residue and X is any amino acid; and which comprises at least one of the following amino acid substitutions with reference to the position numbering of SEQ ID NO:2: Leucine (L) to Phenylalanine (F) at position 578 Asparagine (N) to Serine (S) at position 617 Asparagine (N) to Serine (S) at position 826 Leucine (L) to Phenylalanine (F) at position 857 and Isoleucine (I) to Valine (V) at position 1000 such that an IBV virus comprising the S protein has extended tissue tropism. The present invention also provides a virus comprising such an S protein.

18 Claims, 5 Drawing Sheets

(56) References Cited

OTHER PUBLICATIONS

Madu et al., Heparan sulfate is a selective attachment factor for the avian coronavirus infectious bronchitis virus Beaudette, *Avian Diseases*, 51:45-51 (2007).
Tatusova et al., BLAST 2 Sequences, a new tool for comparing protein and nucleotide sequences, *FEMS Microbiol. Lett.*, 174(2): 247-50 (1999).
Tatusova et al., Erratum to "BLAST 2 Sequences, a new tool for comparing protein and nucleotide sequences", *FEMS Microbiol. Lett.*, 177(1): 187-8 (1999).
Wei et al., Development and characterization of a recombinant infectious bronchitis virus expressing the ectodomain region of S1 gene H120 strain, *Appl. Microbiol. Biotechnol.*, 98(4):1727-35 (2014).
Yamada et al., Acquisition of Cell-Cell Fusion Activity by Amino Acid Substitutions in Spike Protein Determines the Infectivity of a Coronavirus in Cultured Cells, *PLoS One*, 4(7):e6130 (2009).
Yamada et al., Proteolytic activation of the spike protein at a novel RRRR/S motif is implicated in furin-dependent entry, syncytium formation, and infectivity of coronavirus infectious bronchitis virus in cultured cells, *J. Virol.*, 83(17):8744-58 (2009).
International Search Report and Written Opinion of the International Search Authority, European Patent Office, dated Jul. 29, 2014.
International Preliminary Report on Patentability, International Bureau of WIPO, dated Nov. 3, 2015.

\* cited by examiner

SEQUENCE LISTING

```
<160> NUMBER OF SEQ ID NOS: 14

<210> SEQ ID NO 1
<211> LENGTH: 1162
<212> TYPE: PRT
<213> ORGANISM: Infectious bronchitis virus (IBV)

<400> SEQUENCE: 1

Met Leu Val Thr Pro Leu Leu Val Thr Leu Leu Cys Ala Leu Cys
1               5                   10                  15

Ser Ala Val Leu Tyr Asp Ser Ser Tyr Val Tyr Tyr Tyr Gln Ser
                20                  25                  30

Ala Phe Arg Pro Pro Ser Gly Trp His Leu Gln Gly Gly Ala Tyr Ala
            35                  40                  45

Val Val Asn Ile Ser Ser Glu Phe Asn Asn Ala Gly Ser Ser Ser Gly
        50                  55                  60

Cys Thr Val Gly Ile Ile His Gly Gly Arg Val Val Asn Ala Ser Ser
65                  70                  75                  80

Ile Ala Met Thr Ala Pro Ser Ser Gly Met Ala Trp Ser Ser Ser Gln
                85                  90                  95

Phe Cys Thr Ala His Cys Asn Phe Ser Asp Thr Thr Val Phe Val Thr
            100                 105                 110

His Cys Tyr Lys His Gly Gly Cys Pro Leu Thr Gly Met Leu Gln Gln
        115                 120                 125

Asn Leu Ile Arg Val Ser Ala Met Lys Asn Gly Gln Leu Phe Tyr Asn
    130                 135                 140

Leu Thr Val Ser Val Ala Lys Tyr Pro Thr Phe Arg Ser Phe Gln Cys
145                 150                 155                 160

Val Asn Asn Leu Thr Ser Val Tyr Leu Asn Gly Asp Leu Val Tyr Thr
                165                 170                 175

Ser Asn Glu Thr Ile Asp Val Thr Ser Ala Gly Val Tyr Phe Lys Ala
            180                 185                 190

Gly Gly Pro Ile Thr Tyr Lys Val Met Arg Glu Val Lys Ala Leu Ala
        195                 200                 205

Tyr Phe Val Asn Gly Thr Ala Gln Asp Val Ile Leu Cys Asp Gly Ser
    210                 215                 220

Pro Arg Gly Leu Leu Ala Cys Gln Tyr Asn Thr Gly Asn Phe Ser Asp
225                 230                 235                 240
```

-continued

```
Gly Phe Tyr Pro Phe Thr Asn Ser Ser Leu Val Lys Gln Lys Phe Ile
                    245                 250                 255

Val Tyr Arg Glu Asn Ser Val Asn Thr Thr Cys Thr Leu His Asn Phe
                260                 265                 270

Ile Phe His Asn Glu Thr Gly Ala Asn Pro Asn Pro Ser Gly Val Gln
            275                 280                 285

Asn Ile Gln Thr Tyr Gln Thr Lys Thr Ala Gln Ser Gly Tyr Tyr Asn
        290                 295                 300

Phe Asn Phe Ser Phe Leu Ser Ser Phe Val Tyr Lys Glu Ser Asn Phe
305                 310                 315                 320

Met Tyr Gly Ser Tyr His Pro Ser Cys Lys Phe Arg Leu Glu Thr Ile
                325                 330                 335

Asn Asn Gly Leu Trp Phe Asn Ser Leu Ser Val Ser Ile Ala Tyr Gly
                340                 345                 350

Pro Leu Gln Gly Gly Cys Lys Gln Ser Val Phe Lys Gly Arg Ala Thr
            355                 360                 365

Cys Cys Tyr Ala Tyr Ser Tyr Gly Gly Pro Ser Leu Cys Lys Gly Val
        370                 375                 380

Tyr Ser Gly Glu Leu Asp His Asn Phe Glu Cys Gly Leu Leu Val Tyr
385                 390                 395                 400

Val Thr Lys Ser Gly Gly Ser Arg Ile Gln Thr Ala Thr Glu Pro Pro
                405                 410                 415

Val Ile Thr Gln Asn Asn Tyr Asn Asn Ile Thr Leu Asn Thr Cys Val
            420                 425                 430

Asp Tyr Asn Ile Tyr Gly Arg Thr Gly Gln Gly Phe Ile Thr Asn Val
        435                 440                 445

Thr Asp Ser Ala Val Ser Tyr Asn Tyr Leu Ala Asp Ala Gly Leu Ala
    450                 455                 460

Ile Leu Asp Thr Ser Gly Ser Ile Asp Ile Phe Val Val Gln Gly Glu
465                 470                 475                 480

Tyr Gly Leu Asn Tyr Tyr Lys Val Asn Pro Cys Glu Asp Val Asn Gln
                485                 490                 495

Gln Phe Val Val Ser Gly Gly Lys Leu Val Gly Ile Leu Thr Ser Arg
            500                 505                 510

Asn Glu Thr Gly Ser Gln Leu Leu Glu Asn Gln Phe Tyr Ile Lys Ile
        515                 520                 525

Thr Asn Gly Thr Arg Arg Phe Arg Arg Ser Ile Thr Glu Asn Val Ala
    530                 535                 540

Asn Cys Pro Tyr Val Ser Tyr Gly Lys Phe Cys Ile Lys Pro Asp Gly
545                 550                 555                 560

Ser Ile Ala Thr Ile Val Pro Lys Gln Leu Glu Gln Phe Val Ala Pro
                565                 570                 575

Leu Phe Asn Val Thr Glu Asn Val Leu Ile Pro Asn Ser Phe Asn Leu
            580                 585                 590

Thr Val Thr Asp Glu Tyr Ile Gln Thr Arg Met Asp Lys Val Gln Ile
        595                 600                 605

Asn Cys Leu Gln Tyr Val Cys Gly Ser Ser Leu Asp Cys Arg Lys Leu
    610                 615                 620

Phe Gln Gln Tyr Gly Pro Val Cys Asp Asn Ile Leu Ser Val Val Asn
625                 630                 635                 640

Ser Val Gly Gln Lys Glu Asp Met Glu Leu Leu Asn Phe Tyr Ser Ser
                645                 650                 655
```

-continued

Thr Lys Pro Ala Gly Phe Asn Thr Pro Val Leu Ser Asn Val Ser Thr
            660                 665                 670

Gly Glu Phe Asn Ile Ser Leu Leu Thr Asn Pro Ser Ser Arg Arg
        675                 680                 685

Lys Arg Ser Leu Ile Glu Asp Leu Leu Phe Thr Ser Val Glu Ser Val
690                 695                 700

Gly Leu Pro Thr Asn Asp Ala Tyr Lys Asn Cys Thr Ala Gly Pro Leu
705                 710                 715                 720

Gly Phe Phe Lys Asp Leu Ala Cys Ala Arg Glu Tyr Asn Gly Leu Leu
                725                 730                 735

Val Leu Pro Pro Ile Ile Thr Ala Glu Met Gln Ala Leu Tyr Thr Ser
            740                 745                 750

Ser Leu Val Ala Ser Met Ala Phe Gly Gly Ile Thr Ala Ala Gly Ala
        755                 760                 765

Ile Pro Phe Ala Thr Gln Leu Gln Ala Arg Ile Asn His Leu Gly Ile
770                 775                 780

Thr Gln Ser Leu Leu Leu Lys Asn Gln Glu Lys Ile Ala Ala Ser Phe
785                 790                 795                 800

Asn Lys Ala Ile Gly His Met Gln Glu Gly Phe Arg Ser Thr Ser Leu
                805                 810                 815

Ala Leu Gln Gln Ile Gln Asp Val Val Ser Lys Gln Ser Ala Ile Leu
            820                 825                 830

Thr Glu Thr Met Ala Ser Leu Asn Lys Asn Phe Gly Ala Ile Ser Ser
        835                 840                 845

Val Ile Gln Glu Ile Tyr Gln Gln Phe Asp Ala Ile Gln Ala Asn Ala
850                 855                 860

Gln Val Asp Arg Leu Ile Thr Gly Arg Leu Ser Ser Leu Ser Val Leu
865                 870                 875                 880

Ala Ser Ala Lys Gln Ala Glu Tyr Ile Arg Val Ser Gln Gln Arg Glu
                885                 890                 895

Leu Ala Thr Gln Lys Ile Asn Glu Cys Val Lys Ser Gln Ser Ile Arg
            900                 905                 910

Tyr Ser Phe Cys Gly Asn Gly Arg His Val Leu Thr Ile Pro Gln Asn
        915                 920                 925

Ala Pro Asn Gly Ile Val Phe Ile His Phe Ser Tyr Thr Pro Asp Ser
930                 935                 940

Phe Val Asn Val Thr Ala Ile Val Gly Phe Cys Val Lys Pro Ala Asn
945                 950                 955                 960

Ala Ser Gln Tyr Ala Ile Val Pro Ala Asn Gly Arg Gly Ile Phe Ile
                965                 970                 975

Gln Val Asn Gly Ser Tyr Tyr Ile Thr Ala Arg Asp Met Tyr Met Pro
            980                 985                 990

Arg Ala Ile Thr Ala Gly Asp Val  Val Thr Leu Thr Ser  Cys Gln Ala
        995                 1000                1005

Asn Tyr Val Ser Val Asn Lys  Thr Val Ile Thr Thr  Phe Val Asp
        1010                1015                1020

Asn Asp Asp Phe Asp Phe Asn  Asp Glu Leu Ser Lys  Trp Trp Asn
        1025                1030                1035

Asp Thr Lys His Glu Leu Pro  Asp Phe Asp Lys Phe  Asn Tyr Thr
        1040                1045                1050

Val Pro Ile Leu Asp Ile Asp  Ser Glu Ile Asp Arg  Ile Gln Gly
        1055                1060                1065

Val Ile Gln Gly Leu Asn Asp  Ser Leu Ile Asp Leu  Glu Lys Leu

```
                1070                1075                1080
Ser Ile Leu Lys Thr Tyr Ile Lys Trp Pro Trp Tyr Val Trp Leu
            1085                1090                1095

Ala Ile Ala Phe Ala Thr Ile Ile Phe Ile Leu Ile Leu Gly Trp
    1100                1105                1110

Val Phe Phe Met Thr Gly Cys Cys Gly Cys Cys Cys Gly Cys Phe
    1115                1120                1125

Gly Ile Met Pro Leu Met Ser Lys Cys Gly Lys Lys Ser Ser Tyr
    1130                1135                1140

Tyr Thr Thr Phe Asp Asn Asp Val Val Thr Glu Gln Tyr Arg Pro
    1145                1150                1155

Lys Lys Ser Val
    1160

<210> SEQ ID NO 2
<211> LENGTH: 1162
<212> TYPE: PRT
<213> ORGANISM: Infectious bronchitis virus (IBV)

<400> SEQUENCE: 2

Met Leu Val Thr Pro Leu Leu Val Thr Leu Leu Cys Val Leu Cys
1               5                   10                  15

Ser Ala Ala Leu Tyr Asp Ser Ser Ser Tyr Val Tyr Tyr Gln Ser
            20                  25                  30

Ala Phe Arg Pro Pro Asn Gly Trp His Leu His Gly Gly Ala Tyr Ala
        35                  40                  45

Val Val Asn Ile Ser Ser Glu Ser Asn Asn Ala Gly Ser Ser Pro Gly
    50                  55                  60

Cys Ile Val Gly Thr Ile His Gly Gly Arg Val Val Asn Ala Ser Ser
65                  70                  75                  80

Ile Ala Met Thr Ala Pro Ser Ser Gly Met Ala Trp Ser Ser Ser Gln
                85                  90                  95

Phe Cys Thr Ala His Cys Asn Phe Ser Asp Thr Thr Val Phe Val Thr
            100                 105                 110

His Cys Tyr Lys Tyr Asp Gly Cys Pro Ile Thr Gly Met Leu Gln Lys
        115                 120                 125

Asn Phe Leu Arg Val Ser Ala Met Lys Asn Gly Gln Leu Phe Tyr Asn
    130                 135                 140

Leu Thr Val Ser Val Ala Lys Tyr Pro Thr Phe Lys Ser Phe Gln Cys
145                 150                 155                 160

Val Asn Asn Leu Thr Ser Val Tyr Leu Asn Gly Asp Leu Val Tyr Thr
                165                 170                 175

Ser Asn Glu Thr Thr Asp Val Thr Ser Ala Gly Val Tyr Phe Lys Ala
            180                 185                 190

Gly Gly Pro Ile Thr Tyr Lys Val Met Arg Lys Val Lys Ala Leu Ala
        195                 200                 205

Tyr Phe Val Asn Gly Thr Ala Gln Asp Val Ile Leu Cys Asp Gly Ser
    210                 215                 220

Pro Arg Gly Leu Leu Ala Cys Gln Tyr Asn Thr Gly Asn Phe Ser Asp
225                 230                 235                 240

Gly Phe Tyr Pro Phe Ile Asn Ser Ser Leu Val Lys Gln Lys Phe Ile
                245                 250                 255

Val Tyr Arg Glu Asn Ser Val Asn Thr Thr Phe Thr Leu His Asn Phe
            260                 265                 270
```

```
Thr Phe His Asn Glu Thr Gly Ala Asn Pro Asn Pro Ser Gly Val Gln
            275                 280                 285

Asn Ile Leu Thr Tyr Gln Thr Gln Thr Ala Gln Ser Gly Tyr Tyr Asn
        290                 295                 300

Phe Asn Phe Ser Phe Leu Ser Ser Phe Val Tyr Lys Glu Ser Asn Phe
305                 310                 315                 320

Met Tyr Gly Ser Tyr His Pro Ser Cys Asn Phe Arg Leu Glu Thr Ile
                325                 330                 335

Asn Asn Gly Leu Trp Phe Asn Ser Leu Ser Val Ser Ile Ala Tyr Gly
            340                 345                 350

Pro Leu Gln Gly Gly Cys Lys Gln Ser Val Phe Ser Gly Arg Ala Thr
            355                 360                 365

Cys Cys Tyr Ala Tyr Ser Tyr Gly Gly Pro Ser Leu Cys Lys Gly Val
    370                 375                 380

Tyr Ser Gly Glu Leu Asp Leu Asn Phe Glu Cys Gly Leu Leu Val Tyr
385                 390                 395                 400

Val Thr Lys Ser Gly Gly Ser Arg Ile Gln Thr Ala Thr Glu Pro Pro
                405                 410                 415

Val Ile Thr Arg His Asn Tyr Asn Asn Ile Thr Leu Asn Thr Cys Val
            420                 425                 430

Asp Tyr Asn Ile Tyr Gly Arg Thr Gly Gln Gly Phe Ile Thr Asn Val
            435                 440                 445

Thr Asp Ser Ala Val Ser Tyr Asn Tyr Leu Ala Asp Ala Gly Leu Ala
    450                 455                 460

Ile Leu Asp Thr Ser Gly Ser Ile Asp Ile Phe Val Val Gln Gly Glu
465                 470                 475                 480

Tyr Gly Leu Thr Tyr Tyr Lys Val Asn Pro Cys Glu Asp Val Asn Gln
                485                 490                 495

Gln Phe Val Val Ser Gly Gly Lys Leu Val Gly Ile Leu Thr Ser Arg
            500                 505                 510

Asn Glu Thr Gly Ser Gln Leu Leu Glu Asn Gln Phe Tyr Ile Lys Ile
        515                 520                 525

Thr Asn Gly Thr Arg Arg Phe Arg Arg Ser Ile Thr Glu Asn Val Ala
    530                 535                 540

Asn Cys Pro Tyr Val Ser Tyr Gly Lys Phe Cys Ile Lys Pro Asp Gly
545                 550                 555                 560

Ser Ile Ala Thr Ile Val Pro Lys Gln Leu Glu Gln Phe Val Ala Pro
                565                 570                 575

Leu Leu Asn Val Thr Glu Asn Val Leu Ile Pro Asn Ser Phe Asn Leu
            580                 585                 590

Thr Val Thr Asp Glu Tyr Ile Gln Thr Arg Met Asp Lys Val Gln Ile
            595                 600                 605

Asn Cys Leu Gln Tyr Val Cys Gly Asn Ser Leu Asp Cys Arg Asp Leu
    610                 615                 620

Phe Gln Gln Tyr Gly Pro Val Cys Asp Asn Ile Leu Ser Val Val Asn
625                 630                 635                 640

Ser Ile Gly Gln Lys Glu Asp Met Glu Leu Leu Asn Phe Tyr Ser Ser
                645                 650                 655

Thr Lys Pro Ala Gly Phe Asn Thr Pro Phe Leu Ser Asn Val Ser Thr
            660                 665                 670

Gly Glu Phe Asn Ile Ser Leu Leu Leu Thr Thr Pro Ser Ser Pro Arg
            675                 680                 685

Arg Arg Ser Phe Ile Glu Asp Leu Leu Phe Thr Ser Val Glu Ser Val
```

-continued

```
            690             695             700
Gly Leu Pro Thr Asp Asp Ala Tyr Lys Asn Cys Thr Ala Gly Pro Leu
705             710             715             720

Gly Phe Leu Lys Asp Leu Ala Cys Ala Arg Glu Tyr Asn Gly Leu Leu
            725             730             735

Val Leu Pro Pro Ile Ile Thr Ala Glu Met Gln Thr Leu Tyr Thr Ser
            740             745             750

Ser Leu Val Ala Ser Met Ala Phe Gly Gly Ile Thr Ala Ala Gly Ala
            755             760             765

Ile Pro Phe Ala Thr Gln Leu Gln Ala Arg Ile Asn His Leu Gly Ile
770             775             780

Thr Gln Ser Leu Leu Leu Lys Asn Gln Glu Lys Ile Ala Ala Ser Phe
785             790             795             800

Asn Lys Ala Ile Gly Arg Met Gln Glu Gly Phe Arg Ser Thr Ser Leu
            805             810             815

Ala Leu Gln Gln Ile Gln Asp Val Val Asn Lys Gln Ser Ala Ile Leu
            820             825             830

Thr Glu Thr Met Ala Ser Leu Asn Lys Asn Phe Gly Ala Ile Ser Ser
            835             840             845

Val Ile Gln Glu Ile Tyr Gln Gln Leu Asp Ala Ile Gln Ala Asn Ala
850             855             860

Gln Val Asp Arg Leu Ile Thr Gly Arg Leu Ser Ser Leu Ser Val Leu
865             870             875             880

Ala Ser Ala Lys Gln Ala Glu His Ile Arg Val Ser Gln Gln Arg Glu
            885             890             895

Leu Ala Thr Gln Lys Ile Asn Glu Cys Val Lys Ser Gln Ser Ile Arg
            900             905             910

Tyr Ser Phe Cys Gly Asn Gly Arg His Val Leu Thr Ile Pro Gln Asn
            915             920             925

Ala Pro Asn Gly Ile Val Phe Ile His Phe Ser Tyr Thr Pro Asp Ser
            930             935             940

Phe Val Asn Val Thr Ala Ile Val Gly Phe Cys Val Lys Pro Ala Asn
945             950             955             960

Ala Ser Gln Tyr Ala Ile Val Pro Ala Asn Gly Arg Gly Ile Phe Ile
            965             970             975

Gln Val Asn Gly Ser Tyr Tyr Ile Thr Ala Arg Asp Met Tyr Met Pro
            980             985             990

Arg Ala Ile Thr Ala Gly Asp Ile Val Thr Leu Thr Ser Cys Gln Ala
            995             1000            1005

Asn Tyr Val Ser Val Asn Lys Thr Val Ile Thr Thr Phe Val Asp
    1010            1015            1020

Asn Asp Asp Phe Asp Phe Asn Asp Glu Leu Ser Lys Trp Trp Asn
    1025            1030            1035

Asp Thr Lys His Glu Leu Pro Asp Phe Asp Lys Phe Asn Tyr Thr
    1040            1045            1050

Val Pro Ile Leu Asp Ile Asp Ser Glu Ile Asp Arg Ile Gln Gly
    1055            1060            1065

Val Ile Gln Gly Leu Asn Asp Ser Leu Ile Asp Leu Glu Lys Leu
    1070            1075            1080

Ser Ile Leu Lys Thr Tyr Ile Lys Trp Pro Trp Tyr Val Trp Leu
    1085            1090            1095

Ala Ile Ala Phe Ala Thr Ile Ile Phe Ile Leu Ile Leu Gly Trp
    1100            1105            1110
```

```
Val Phe Phe Met Thr Gly Cys Cys Gly Cys Cys Gly Cys Phe
    1115                1120                1125

Gly Ile Met Pro Leu Met Ser Lys Cys Gly Lys Lys Ser Ser Tyr
    1130                1135                1140

Tyr Thr Thr Phe Asp Asn Asp Val Val Thr Glu Gln Asn Arg Pro
    1145                1150                1155

Lys Lys Ser Val
    1160

<210> SEQ ID NO 3
<211> LENGTH: 6
<212> TYPE: PRT
<213> ORGANISM: Artificial Sequence
<220> FEATURE:
<223> OTHER INFORMATION: Sequence motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (2)..(3)
<223> OTHER INFORMATION: Xaa is a basic amino acid residue (Arg, His,
      Lys)
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa is a basic amino acid residue (Arg, His,
      Lys)
<220> FEATURE:
<221> NAME/KEY: misc_feature
<222> LOCATION: (6)..(6)
<223> OTHER INFORMATION: Xaa can be any naturally occurring amino acid

<400> SEQUENCE: 3

Xaa Xaa Xaa Xaa Xaa Xaa
1               5

<210> SEQ ID NO 4
<211> LENGTH: 6
<212> TYPE: PRT
<213> ORGANISM: Infectious bronchitis virus (IBV)

<400> SEQUENCE: 4

Ser Arg Arg Lys Arg Ser
1               5

<210> SEQ ID NO 5
<211> LENGTH: 6
<212> TYPE: PRT
<213> ORGANISM: Infectious bronchitis virus (IBV)

<400> SEQUENCE: 5

Ser Arg Arg Arg Arg Ser
1               5

<210> SEQ ID NO 6
<211> LENGTH: 9
<212> TYPE: PRT
<213> ORGANISM: Infectious bronchitis virus (IBV)

<400> SEQUENCE: 6

Ser Arg Arg Lys Arg Ser Leu Ile Glu
```

```
<210> SEQ ID NO 7
<211> LENGTH: 9
<212> TYPE: PRT
<213> ORGANISM: Infectious bronchitis virus (IBV)

<400> SEQUENCE: 7

Ser Arg Arg Arg Arg Ser Val Ile Glu
1               5

<210> SEQ ID NO 8
<211> LENGTH: 1153
<212> TYPE: PRT
<213> ORGANISM: Infectious bronchitis virus (IBV)

<400> SEQUENCE: 8

Met Leu Val Thr Pro Leu Leu Val Thr Leu Leu Cys Val Leu Cys
1               5                   10                  15

Ser Ala Ala Leu Tyr Asp Ser Ser Tyr Val Tyr Tyr Tyr Gln Ser
                20                  25                  30

Ala Phe Arg Pro Pro Asn Gly Trp His Leu His Gly Gly Ala Tyr Ala
        35                  40                  45

Val Val Asn Ile Ser Ser Glu Ser Asn Asn Ala Gly Ser Ser Pro Gly
            50                  55                  60

Cys Ile Val Gly Thr Ile His Gly Gly Arg Val Val Asn Ala Ser Ser
65                  70                  75                  80

Ile Ala Met Thr Ala Pro Ser Ser Gly Met Ala Trp Ser Ser Ser Gln
                85                  90                  95

Phe Cys Thr Ala His Cys Asn Phe Ser Asp Thr Thr Val Phe Val Thr
                100                 105                 110

His Cys Tyr Lys Tyr Asp Gly Cys Pro Ile Thr Gly Met Leu Gln Lys
            115                 120                 125

Asn Phe Leu Arg Val Ser Ala Met Lys Asn Gly Gln Leu Phe Tyr Asn
        130                 135                 140

Leu Thr Val Ser Val Ala Lys Tyr Pro Thr Phe Lys Ser Phe Gln Cys
145                 150                 155                 160

Val Asn Asn Leu Thr Ser Val Tyr Leu Asn Gly Asp Leu Val Tyr Thr
                165                 170                 175

Ser Asn Glu Thr Thr Asp Val Thr Ser Ala Gly Val Tyr Phe Lys Ala
                180                 185                 190

Gly Gly Pro Ile Thr Tyr Lys Val Met Arg Glu Val Lys Ala Leu Ala
            195                 200                 205

Tyr Phe Val Asn Gly Thr Ala Gln Asp Val Ile Leu Cys Asp Gly Ser
        210                 215                 220

Pro Arg Gly Leu Leu Ala Cys Gln Tyr Asn Thr Gly Asn Phe Ser Asp
225                 230                 235                 240

Gly Phe Tyr Pro Phe Ile Asn Ser Ser Leu Val Lys Gln Lys Phe Ile
                245                 250                 255

Val Tyr Arg Glu Asn Ser Val Asn Thr Thr Phe Thr Leu His Asn Phe
                260                 265                 270

Thr Phe His Asn Glu Thr Gly Ala Asn Pro Asn Pro Ser Gly Val Gln
            275                 280                 285

Asn Ile Gln Thr Tyr Gln Thr Gln Thr Ala Gln Ser Gly Tyr Tyr Asn
        290                 295                 300

Phe Asn Phe Ser Phe Leu Ser Ser Phe Val Tyr Lys Glu Ser Asn Phe
```

-continued

```
             305                 310                 315                 320
        Met Tyr Gly Ser Tyr His Pro Ser Cys Asn Phe Arg Leu Glu Thr Ile
                        325                 330                 335

Asn Asn Gly Leu Trp Phe Asn Ser Leu Ser Val Ser Ile Ala Tyr Gly
                        340                 345                 350

Pro Leu Gln Gly Gly Cys Lys Gln Ser Val Phe Ser Gly Arg Ala Thr
                        355                 360                 365

Cys Cys Tyr Ala Tyr Ser Tyr Gly Gly Pro Ser Leu Cys Lys Gly Val
                370                 375                 380

Tyr Ser Gly Glu Leu Asp Leu Asn Phe Glu Cys Gly Leu Leu Val Tyr
        385                 390                 395                 400

Val Thr Lys Ser Gly Ser Arg Ile Gln Thr Ala Thr Glu Pro Pro
                        405                 410                 415

Val Ile Thr Arg His Asn Tyr Asn Asn Ile Thr Leu Asn Thr Cys Val
                        420                 425                 430

Asp Tyr Asn Ile Tyr Gly Arg Thr Gly Gln Gly Phe Ile Thr Asn Val
                        435                 440                 445

Thr Asp Ser Ala Val Ser Tyr Asn Tyr Leu Ala Asp Ala Gly Leu Ala
                450                 455                 460

Ile Leu Asp Thr Ser Gly Ser Ile Asp Ile Phe Val Val Gln Gly Glu
        465                 470                 475                 480

Tyr Gly Leu Thr Tyr Tyr Lys Val Tyr Pro Cys Glu Asp Val Asn Gln
                        485                 490                 495

Gln Phe Val Val Ser Gly Gly Lys Leu Val Gly Ile Leu Thr Ser Arg
                        500                 505                 510

Asn Glu Thr Gly Ser Gln Leu Leu Glu Asn Gln Phe Tyr Ile Lys Ile
                        515                 520                 525

Thr Asn Gly Thr Arg Arg Phe Arg Arg Ser Ile Thr Glu Asn Val Ala
                        530                 535                 540

Asn Cys Pro Tyr Val Ser Tyr Gly Lys Phe Cys Ile Lys Pro Asp Gly
        545                 550                 555                 560

Ser Ile Ala Thr Ile Val Pro Lys Gln Leu Glu Gln Phe Val Ala Pro
                        565                 570                 575

Leu Leu Asn Val Thr Glu Asn Val Leu Ile Pro Asn Ser Phe Asn Leu
                        580                 585                 590

Thr Val Thr Asp Glu Tyr Ile Gln Thr Arg Met Asp Lys Val Gln Ile
                        595                 600                 605

Asn Cys Met Gln Tyr Val Cys Gly Asn Ser Leu Asp Cys Arg Asp Leu
                610                 615                 620

Phe Gln Gln Tyr Gly Pro Val Cys Asp Asn Ile Leu Ser Val Val Asn
        625                 630                 635                 640

Ser Ile Gly Gln Lys Glu Asp Met Glu Leu Leu Asn Phe Tyr Ser Ser
                        645                 650                 655

Thr Lys Pro Ala Gly Phe Asn Thr Pro Phe Leu Ser Asn Val Ser Thr
                        660                 665                 670

Gly Glu Phe Asn Ile Ser Leu Leu Leu Thr Thr Pro Ser Ser Pro Arg
                        675                 680                 685

Arg Arg Ser Phe Ile Glu Asp Leu Leu Phe Thr Ser Val Glu Ser Val
                        690                 695                 700

Gly Leu Pro Thr Asp Asp Ala Tyr Lys Asn Cys Thr Ala Gly Pro Leu
        705                 710                 715                 720

Gly Phe Leu Lys Asp Leu Ala Cys Ala Arg Glu Tyr Asn Gly Leu Leu
                        725                 730                 735
```

-continued

```
Val Leu Pro Pro Ile Ile Thr Ala Glu Met Gln Thr Leu Tyr Thr Ser
            740                 745                 750

Ser Leu Val Ala Ser Met Ala Phe Gly Gly Ile Thr Ala Ala Gly Ala
            755                 760                 765

Ile Pro Phe Ala Thr Gln Leu Gln Ala Arg Ile Asn His Leu Gly Ile
            770                 775                 780

Thr Gln Ser Leu Leu Leu Lys Asn Gln Glu Lys Ile Ala Ala Ser Phe
785                 790                 795                 800

Asn Lys Ala Ile Gly Arg Met Gln Glu Gly Phe Arg Ser Thr Ser Leu
            805                 810                 815

Ala Leu Gln Gln Ile Gln Asp Val Val Asn Lys Gln Ser Ala Ile Leu
            820                 825                 830

Thr Glu Thr Met Ala Ser Leu Asn Lys Asn Phe Gly Ala Ile Ser Ser
            835                 840                 845

Met Ile Gln Glu Ile Tyr Gln Gln Leu Asp Ala Ile Gln Ala Asn Ala
            850                 855                 860

Gln Val Asp Arg Leu Ile Thr Gly Arg Leu Ser Ser Leu Ser Val Leu
865                 870                 875                 880

Ala Ser Ala Lys Gln Ala Glu His Ile Arg Val Ser Gln Gln Arg Glu
            885                 890                 895

Leu Ala Thr Gln Lys Ile Asn Glu Cys Val Lys Ser Gln Ser Ile Arg
            900                 905                 910

Tyr Ser Phe Cys Gly Asn Gly Arg His Val Leu Thr Ile Pro Gln Asn
            915                 920                 925

Ala Pro Asn Gly Ile Val Phe Ile His Phe Ser Tyr Thr Pro Asp Ser
            930                 935                 940

Phe Val Asn Val Thr Ala Ile Val Gly Phe Cys Val Lys Pro Ala Asn
945                 950                 955                 960

Ala Ser Gln Tyr Ala Ile Val Pro Ala Asn Gly Arg Gly Ile Phe Ile
            965                 970                 975

Gln Val Asn Gly Ser Tyr Tyr Ile Thr Ala Arg Asp Met Tyr Met Pro
            980                 985                 990

Arg Ala Ile Thr Ala Gly Asp Ile Val Thr Leu Thr Ser Cys Gln Ala
            995                 1000                1005

Asn Tyr Val Ser Val Asn Lys Thr Val Ile Thr Thr Phe Val Asp
            1010                1015                1020

Asn Asp Asp Phe Asp Phe Asn Asp Glu Leu Ser Lys Trp Trp Asn
            1025                1030                1035

Asp Thr Lys His Glu Leu Pro Asp Phe Asp Lys Phe Asn Tyr Thr
            1040                1045                1050

Val Pro Ile Leu Asp Ile Asp Ser Glu Ile Asp Arg Ile Gln Gly
            1055                1060                1065

Val Ile Gln Gly Leu Asn Asp Ser Leu Ile Asp Leu Glu Lys Leu
            1070                1075                1080

Ser Ile Leu Lys Thr Tyr Ile Lys Trp Pro Trp Tyr Val Trp Leu
            1085                1090                1095

Ala Ile Ala Phe Ala Thr Ile Ile Phe Ile Leu Ile Leu Gly Trp
            1100                1105                1110

Val Phe Phe Met Thr Gly Cys Cys Gly Cys Cys Cys Gly Cys Phe
            1115                1120                1125

Gly Ile Met Pro Leu Met Ser Lys Cys Gly Lys Lys Ser Ser Tyr
            1130                1135                1140
```

```
Tyr Thr Thr Phe Asp Asn Asp  Val Val Thr
    1145                1150
```

<210> SEQ ID NO 9
<211> LENGTH: 1162
<212> TYPE: PRT
<213> ORGANISM: Infectious bronchitis virus (IBV)

<400> SEQUENCE: 9

```
Met Leu Val Thr Pro Leu Leu Val Thr Leu Leu Cys Ala Leu Cys
1               5                   10                  15

Ser Ala Ala Leu Tyr Asp Ser Ser Tyr Val Tyr Tyr Tyr Gln Ser
                20                  25                  30

Ala Phe Arg Pro Pro Asp Gly Trp His Leu His Gly Gly Ala Tyr Ala
        35                  40                  45

Val Val Asn Ile Ser Ser Glu Ser Asn Asn Ala Gly Ser Ser Ser Gly
    50                  55                  60

Cys Thr Val Gly Ile Ile His Gly Gly Arg Val Val Asn Ala Ser Ser
65                  70                  75                  80

Ile Ala Met Thr Ala Pro Ser Ser Gly Met Ala Trp Ser Ser Ser Gln
                85                  90                  95

Phe Cys Thr Ala Tyr Cys Asn Phe Ser Asp Thr Thr Val Phe Val Thr
                100                 105                 110

His Cys Tyr Lys His Val Gly Cys Pro Ile Thr Gly Met Leu Gln Gln
                115                 120                 125

His Ser Ile Arg Val Ser Ala Met Lys Asn Gly Gln Leu Phe Tyr Asn
    130                 135                 140

Leu Thr Val Ser Val Ala Lys Tyr Pro Thr Phe Lys Ser Phe Gln Cys
145                 150                 155                 160

Val Asn Asn Leu Thr Ser Val Tyr Leu Asn Gly Asp Leu Val Tyr Thr
                165                 170                 175

Ser Asn Glu Thr Thr Asp Val Thr Ser Ala Gly Val Tyr Phe Lys Ala
                180                 185                 190

Gly Gly Pro Ile Thr Tyr Lys Val Met Arg Glu Val Arg Ala Leu Ala
                195                 200                 205

Tyr Phe Val Asn Gly Thr Ala Gln Asp Val Ile Leu Cys Asp Gly Ser
    210                 215                 220

Pro Arg Gly Leu Leu Ala Cys Gln Tyr Asn Thr Gly Asn Phe Ser Asp
225                 230                 235                 240

Gly Phe Tyr Pro Phe Thr Asn Ser Ser Leu Val Lys Gln Lys Phe Ile
                245                 250                 255

Val Tyr Arg Glu Asn Ser Val Asn Thr Thr Phe Thr Leu His Asn Phe
                260                 265                 270

Thr Phe His Asn Glu Thr Gly Ala Asn Pro Asn Pro Ser Gly Val Gln
    275                 280                 285

Asn Ile Gln Thr Tyr Gln Thr Gln Thr Ala Gln Ser Gly Tyr Tyr Asn
    290                 295                 300

Phe Asn Phe Ser Phe Leu Ser Ser Phe Val Tyr Lys Glu Ser Asn Phe
305                 310                 315                 320

Met Tyr Gly Ser Tyr Tyr Pro Ser Cys Asn Phe Arg Leu Glu Thr Ile
                325                 330                 335

Asn Asn Gly Leu Trp Phe Asn Ser Leu Ser Val Ser Ile Ala Tyr Gly
                340                 345                 350

Pro Leu Gln Gly Gly Cys Lys Gln Ser Val Phe Ser Gly Arg Ala Thr
                355                 360                 365
```

```
Cys Cys Tyr Ala Tyr Ser Tyr Gly Gly Pro Leu Leu Cys Lys Gly Val
    370             375             380

Tyr Ser Gly Glu Leu Asp His Asn Phe Glu Cys Gly Leu Leu Val Tyr
385             390             395                         400

Val Thr Lys Ser Gly Gly Ser Arg Ile Gln Thr Ala Thr Glu Pro Pro
            405             410             415

Val Ile Thr Gln His Asn Tyr Asn Asn Ile Thr Leu Asn Thr Cys Val
            420             425             430

Asp Tyr Asn Ile Tyr Gly Arg Thr Gly Gln Gly Phe Ile Thr Asn Val
            435             440             445

Thr Asp Ser Ala Val Ser Tyr Asn Tyr Leu Ala Asp Ala Gly Leu Ala
        450             455             460

Ile Leu Asp Thr Ser Gly Ser Ile Asp Ile Phe Val Val Gln Ser Glu
465             470             475                         480

Tyr Gly Leu Asn Tyr Tyr Lys Val Asn Pro Cys Glu Asp Val Asn Gln
            485             490             495

Gln Phe Val Val Ser Gly Gly Lys Leu Val Gly Ile Leu Thr Ser Arg
                500             505             510

Asn Glu Thr Gly Ser Gln Leu Leu Glu Asn Gln Phe Tyr Ile Lys Ile
        515             520             525

Thr Asn Gly Thr Arg Arg Phe Arg Arg Ser Ile Thr Glu Ser Val Glu
        530             535             540

Asn Cys Pro Tyr Val Ser Tyr Gly Lys Phe Cys Ile Lys Pro Asp Gly
545             550             555             560

Ser Ile Ala Thr Ile Val Pro Lys Gln Leu Glu Gln Phe Val Ala Pro
            565             570             575

Leu Leu Asn Val Thr Glu Asn Val Leu Ile Pro Asn Ser Phe Asn Leu
        580             585             590

Thr Val Thr Asp Glu Tyr Ile Gln Thr Arg Met Asp Lys Val Gln Ile
            595             600             605

Asn Cys Leu Gln Tyr Ile Cys Gly Asn Ser Leu Glu Cys Arg Asn Leu
610             615             620

Phe Gln Gln Tyr Gly Pro Val Cys Asp Asn Ile Leu Ser Val Val Asn
625             630             635             640

Ser Val Gly Gln Lys Glu Asp Met Glu Leu Leu Asn Phe Tyr Ser Ser
            645             650             655

Thr Lys Pro Ala Gly Phe Asn Thr Pro Val Leu Ser Asn Val Ser Thr
            660             665             670

Gly Glu Phe Asn Ile Ser Leu Phe Leu Thr Thr Pro Ser Ser Pro Arg
            675             680             685

Arg Arg Ser Phe Ile Glu Asp Leu Leu Phe Thr Ser Val Glu Ser Val
        690             695             700

Gly Leu Pro Thr Asp Asp Ala Tyr Lys Asn Cys Thr Ala Gly Pro Leu
705             710             715             720

Gly Phe Leu Lys Asp Leu Val Cys Ala Arg Glu Tyr Asn Gly Leu Leu
            725             730             735

Val Leu Pro Pro Ile Ile Thr Ala Glu Met Gln Thr Leu Tyr Thr Ser
            740             745             750

Ser Leu Val Ala Ser Met Ala Phe Gly Gly Ile Thr Ala Ala Gly Ala
        755             760             765

Ile Pro Phe Ala Thr Gln Leu Gln Ala Arg Ile Asn His Leu Gly Ile
770             775             780
```

```
Thr Gln Ser Leu Leu Leu Lys Asn Gln Glu Lys Ile Ala Ala Ser Phe
785                 790                 795                 800

Asn Lys Ala Ile Gly His Met Gln Glu Gly Phe Arg Ser Thr Ser Leu
            805                 810                 815

Ala Leu Gln Gln Ile Gln Asp Val Val Asn Lys Gln Ser Ala Ile Leu
            820                 825                 830

Thr Glu Thr Met Ala Ser Leu Asn Lys Asn Phe Gly Ala Ile Ser Ser
        835                 840                 845

Val Ile Gln Glu Ile Tyr Gln Gln Leu Asp Ala Ile Gln Ala Asn Ala
850                 855                 860

Gln Val Asp Arg Leu Ile Thr Gly Arg Leu Ser Ser Leu Ser Val Leu
865                 870                 875                 880

Ala Ser Ala Lys Gln Ala Glu Tyr Ile Arg Val Ser Gln Gln Arg Glu
                885                 890                 895

Leu Ala Thr Gln Lys Ile Asn Glu Cys Val Lys Ser Gln Ser Ile Arg
            900                 905                 910

Tyr Ser Phe Cys Gly Asn Gly Arg His Val Leu Thr Ile Pro Gln Asn
            915                 920                 925

Ala Pro Asn Gly Ile Val Phe Ile His Phe Ser Tyr Thr Pro Asp Ser
        930                 935                 940

Phe Val Asn Val Thr Ala Ile Val Gly Phe Cys Val Lys Pro Ala Asn
945                 950                 955                 960

Ala Ser Gln Tyr Ala Ile Val Pro Ala Asn Gly Arg Gly Ile Phe Ile
                965                 970                 975

Gln Val Asn Gly Ser Tyr Tyr Ile Thr Ala Arg Asp Met Tyr Met Pro
            980                 985                 990

Arg Ala Ile Thr Ala Gly Asp Ile Val Thr Leu Thr Ser Cys Gln Val
            995                 1000                1005

Asn Tyr Val Ser Val Asn Lys Thr Val Ile Thr Thr Phe Val Asp
    1010                1015                1020

Asn Asp Asp Phe Asp Phe Asn Asp Glu Leu Ser Lys Trp Trp Asn
    1025                1030                1035

Asp Thr Lys His Glu Leu Pro Asp Phe Asp Lys Phe Asn Tyr Thr
    1040                1045                1050

Val Pro Ile Leu Asp Ile Asp Ser Glu Ile Asp Arg Ile Gln Gly
    1055                1060                1065

Val Ile Gln Gly Leu Asn Asp Ser Leu Ile Asp Leu Glu Lys Leu
    1070                1075                1080

Ser Ile Leu Lys Thr Tyr Ile Lys Trp Pro Trp Tyr Val Trp Leu
    1085                1090                1095

Ala Ile Ala Phe Ala Thr Ile Ile Phe Ile Leu Ile Leu Gly Trp
    1100                1105                1110

Val Phe Phe Met Thr Gly Cys Cys Gly Cys Cys Cys Gly Cys Phe
    1115                1120                1125

Gly Ile Met Pro Leu Met Ser Lys Cys Gly Lys Lys Ser Ser Tyr
    1130                1135                1140

Tyr Thr Thr Phe Asp Asn Asp Val Val Thr Glu Gln Tyr Arg Pro
    1145                1150                1155

Lys Lys Ser Val
    1160

<210> SEQ ID NO 10
<211> LENGTH: 1164
<212> TYPE: PRT
```

<213> ORGANISM: Infectious bronchitis virus (IBV)

<400> SEQUENCE: 10

```
Met Leu Val Lys Ser Leu Phe Leu Val Thr Ile Leu Cys Ala Leu Cys
1               5                   10                  15

Ser Ala Asn Leu Phe Asp Ser Asp Asn Asn Tyr Val Tyr Tyr Tyr Gln
            20                  25                  30

Ser Ala Phe Arg Pro Pro Asn Gly Trp His Leu Gln Gly Gly Ala Tyr
        35                  40                  45

Ala Val Val Asn Ser Thr Asn Tyr Thr Asn Asn Ala Gly Ser Ala His
    50                  55                  60

Gln Cys Thr Val Gly Val Ile Lys Asp Val Tyr Asn Gln Ser Val Ala
65                  70                  75                  80

Ser Ile Ala Met Thr Ala Pro Leu Gln Gly Met Ala Trp Ser Lys Ser
                85                  90                  95

Gln Phe Cys Ser Ala His Cys Asn Phe Ser Glu Ile Thr Val Phe Val
            100                 105                 110

Thr His Cys Tyr Ser Ser Gly Ser Ser Cys Pro Ile Thr Gly Met Ile
        115                 120                 125

Pro Arg Asp His Ile Arg Ile Ser Ala Met Lys Asn Gly Ser Leu Phe
    130                 135                 140

Tyr Asn Leu Thr Val Ser Val Ser Lys Tyr Pro Asn Phe Lys Ser Phe
145                 150                 155                 160

Gln Cys Val Asn Asn Phe Thr Ser Val Tyr Leu Asn Gly Asp Leu Val
                165                 170                 175

Phe Thr Ser Asn Lys Thr Thr Asp Val Thr Ser Ala Gly Val Tyr Phe
            180                 185                 190

Lys Ala Gly Gly Pro Val Asn Tyr Ser Ile Met Lys Glu Phe Lys Val
        195                 200                 205

Leu Ala Tyr Phe Val Asn Gly Thr Ala Gln Asp Val Val Leu Cys Asp
    210                 215                 220

Asn Ser Pro Lys Gly Leu Leu Ala Cys Gln Tyr Asn Thr Gly Asn Phe
225                 230                 235                 240

Ser Asp Gly Phe Tyr Pro Phe Thr Asn Ser Thr Leu Val Arg Glu Lys
                245                 250                 255

Phe Ile Val Tyr Arg Glu Ser Ser Val Asn Thr Thr Leu Ala Leu Thr
            260                 265                 270

Asn Phe Thr Phe Thr Asn Val Ser Asn Ala Gln Pro Asn Ser Gly Gly
        275                 280                 285

Val Asn Thr Phe His Leu Tyr Gln Thr Gln Thr Ala Gln Ser Gly Tyr
    290                 295                 300

Tyr Asn Phe Asn Leu Ser Phe Leu Ser Gln Phe Val Tyr Lys Ala Ser
305                 310                 315                 320

Asp Phe Met Tyr Gly Ser Tyr His Pro Ser Cys Ser Phe Arg Pro Glu
                325                 330                 335

Thr Ile Asn Ser Gly Leu Trp Phe Asn Ser Leu Ser Val Ser Leu Thr
            340                 345                 350

Tyr Gly Pro Leu Gln Gly Gly Cys Lys Gln Ser Val Phe Ser Gly Lys
        355                 360                 365

Ala Thr Cys Cys Tyr Ala Tyr Ser Tyr Lys Gly Pro Met Ala Cys Lys
    370                 375                 380

Gly Val Tyr Ser Gly Glu Leu Ser Thr Asn Phe Glu Cys Gly Leu Leu
385                 390                 395                 400
```

```
Val Tyr Val Thr Lys Ser Asp Gly Ser Arg Ile Gln Thr Arg Thr Glu
            405                 410                 415

Pro Leu Val Leu Thr Gln Tyr Asn Tyr Asn Asn Ile Thr Leu Asp Lys
            420                 425                 430

Cys Val Ala Tyr Asn Ile Tyr Gly Arg Val Gly Gln Gly Phe Ile Thr
            435                 440                 445

Asn Val Thr Asp Ser Ala Ala Asn Phe Ser Tyr Leu Ala Asp Gly Gly
            450                 455                 460

Leu Ala Ile Leu Asp Thr Ser Gly Ala Ile Asp Val Phe Val Val Gln
465                 470                 475                 480

Gly Ile Tyr Gly Leu Asn Tyr Tyr Lys Val Asn Pro Cys Glu Asp Val
                485                 490                 495

Asn Gln Gln Phe Val Val Ser Gly Gly Asn Ile Val Gly Ile Leu Thr
            500                 505                 510

Ser Arg Asn Glu Thr Gly Ser Glu Gln Val Glu Asn Gln Phe Tyr Val
            515                 520                 525

Lys Leu Thr Asn Ser Ser His Arg Arg Arg Ser Ile Gly Gln Asn
            530                 535                 540

Val Thr Ser Cys Pro Tyr Val Ser Tyr Gly Arg Phe Cys Ile Glu Pro
545                 550                 555                 560

Asp Gly Ser Leu Lys Met Ile Val Pro Glu Glu Leu Lys Gln Phe Val
                565                 570                 575

Ala Pro Leu Leu Asn Ile Thr Glu Ser Val Leu Ile Pro Asn Ser Phe
            580                 585                 590

Asn Leu Thr Val Thr Asp Glu Tyr Ile Gln Thr Arg Met Asp Lys Val
            595                 600                 605

Gln Ile Asn Cys Leu Gln Tyr Val Cys Gly Asn Ser Leu Glu Cys Arg
610                 615                 620

Lys Leu Phe Gln Gln Tyr Gly Pro Val Cys Asp Asn Ile Leu Ser Val
625                 630                 635                 640

Val Asn Ser Val Ser Gln Lys Glu Asp Met Glu Leu Leu Ser Phe Tyr
                645                 650                 655

Ser Ser Thr Lys Pro Lys Gly Tyr Asp Thr Pro Val Leu Ser Asn Val
            660                 665                 670

Ser Thr Gly Glu Phe Asn Ile Ser Leu Leu Leu Lys Pro Pro Ser Ser
            675                 680                 685

Pro Ser Gly Arg Ser Phe Ile Glu Asp Leu Leu Phe Thr Ser Val Glu
            690                 695                 700

Thr Val Gly Leu Pro Thr Asp Ala Glu Tyr Lys Lys Cys Thr Ala Gly
705                 710                 715                 720

Pro Leu Gly Thr Leu Lys Asp Leu Ile Cys Ala Arg Glu Tyr Asn Gly
            725                 730                 735

Leu Leu Val Leu Pro Pro Ile Ile Thr Ala Asp Met Gln Thr Met Tyr
            740                 745                 750

Thr Ala Ser Leu Val Gly Ala Met Ala Phe Gly Gly Ile Thr Ser Ala
            755                 760                 765

Ala Ala Ile Pro Phe Ala Thr Gln Ile Gln Ala Arg Ile Asn His Leu
            770                 775                 780

Gly Ile Thr Gln Ser Leu Leu Met Lys Asn Gln Glu Lys Ile Ala Ala
785                 790                 795                 800

Ser Phe Asn Lys Ala Ile Gly His Met Gln Glu Gly Phe Arg Ser Thr
                805                 810                 815

Ser Leu Ala Leu Gln Gln Ile Gln Asp Val Val Asn Lys Gln Ser Ala
```

```
                820                 825                 830
Ile Leu Thr Glu Thr Met Asn Ser Leu Asn Lys Asn Phe Gly Ala Ile
                835                 840                 845

Thr Ser Val Ile Gln Asp Ile Tyr Ala Gln Leu Asp Ala Ile Gln Ala
                850                 855                 860

Asp Ala Gln Val Asp Arg Leu Ile Thr Gly Arg Leu Ser Ser Leu Ser
865                 870                 875                 880

Val Leu Ala Ser Ala Lys Gln Ser Glu Tyr Ile Arg Val Ser Gln Gln
                885                 890                 895

Arg Glu Leu Ala Thr Gln Lys Ile Asn Glu Cys Val Lys Ser Gln Ser
                900                 905                 910

Asn Arg Tyr Gly Phe Cys Gly Ser Gly Arg His Val Leu Ser Ile Pro
                915                 920                 925

Gln Asn Ala Pro Asn Gly Ile Val Phe Ile His Phe Thr Tyr Thr Pro
                930                 935                 940

Glu Ser Phe Val Asn Val Thr Ala Ile Val Gly Phe Cys Val Asn Pro
945                 950                 955                 960

Ala Asn Ala Ser Gln Tyr Ala Ile Val Pro Ala Asn Gly Arg Gly Ile
                965                 970                 975

Phe Ile Gln Val Asn Gly Thr Tyr Tyr Ile Thr Ala Arg Asp Met Tyr
                980                 985                 990

Met Pro Arg Asp Ile Thr Ala Gly Asp Ile Val Thr Leu Thr Ser Cys
                995                 1000                1005

Gln Ala Asn Tyr Val Asn Val Asn Lys Thr Val Ile Thr Thr Phe
                1010                1015                1020

Val Glu Asp Asp Asp Phe Asp Phe Asp Asp Glu Leu Ser Lys Trp
                1025                1030                1035

Trp Asn Asp Thr Lys His Gln Leu Pro Asp Phe Asp Asp Phe Asn
                1040                1045                1050

Tyr Thr Val Pro Ile Leu Asn Ile Ser Gly Glu Ile Asp Tyr Ile
                1055                1060                1065

Gln Gly Val Ile Gln Gly Leu Asn Asp Ser Leu Ile Asn Leu Glu
                1070                1075                1080

Glu Leu Ser Ile Ile Lys Thr Tyr Ile Lys Trp Pro Trp Tyr Val
                1085                1090                1095

Trp Leu Ala Ile Gly Phe Ala Ile Ile Ile Phe Ile Leu Ile Leu
                1100                1105                1110

Gly Trp Val Phe Phe Met Thr Gly Cys Cys Gly Cys Cys Cys Gly
                1115                1120                1125

Cys Phe Gly Ile Ile Pro Leu Met Ser Lys Cys Gly Lys Lys Ser
                1130                1135                1140

Ser Tyr Tyr Thr Thr Phe Asp Asn Asp Val Val Thr Glu Gln Tyr
                1145                1150                1155

Arg Pro Lys Lys Ser Val
                1160

<210> SEQ ID NO 11
<211> LENGTH: 630
<212> TYPE: PRT
<213> ORGANISM: Infectious bronchitis virus (IBV)

<400> SEQUENCE: 11

Arg Arg Phe Arg Arg Ser Ile Thr Glu Asn Val Ala Asn Cys Pro Tyr
1               5                   10                  15
```

-continued

Val Ser Tyr Gly Lys Phe Cys Ile Lys Pro Asp Gly Ser Ile Ala Thr
            20                  25                  30

Ile Val Pro Lys Gln Leu Glu Gln Phe Val Ala Pro Leu Phe Asn Val
            35                  40                  45

Thr Glu Asn Val Leu Ile Pro Asn Ser Phe Asn Leu Thr Val Thr Asp
 50                  55                  60

Glu Tyr Ile Gln Thr Arg Met Asp Lys Val Gln Ile Asn Cys Leu Gln
 65                  70                  75                  80

Tyr Val Cys Gly Ser Ser Leu Asp Cys Arg Lys Leu Phe Gln Gln Tyr
                85                  90                  95

Gly Pro Val Cys Asp Asn Ile Leu Ser Val Val Asn Ser Val Gly Gln
                100                 105                 110

Lys Glu Asp Met Glu Leu Leu Asn Phe Tyr Ser Ser Thr Lys Pro Ala
            115                 120                 125

Gly Phe Asn Thr Pro Val Leu Ser Asn Val Ser Thr Gly Glu Phe Asn
130                 135                 140

Ile Ser Leu Leu Leu Thr Asn Pro Ser Ser Arg Arg Lys Arg Ser Leu
145                 150                 155                 160

Ile Glu Asp Leu Leu Phe Thr Ser Val Glu Ser Val Gly Leu Pro Thr
                165                 170                 175

Asn Asp Ala Tyr Lys Asn Cys Thr Ala Gly Pro Leu Gly Phe Phe Lys
            180                 185                 190

Asp Leu Ala Cys Ala Arg Glu Tyr Asn Gly Leu Leu Val Leu Pro Pro
            195                 200                 205

Ile Ile Thr Ala Glu Met Gln Ala Leu Tyr Thr Ser Ser Leu Val Ala
210                 215                 220

Ser Met Ala Phe Gly Gly Ile Thr Ala Ala Gly Ala Ile Pro Phe Ala
225                 230                 235                 240

Thr Gln Leu Gln Ala Arg Ile Asn His Leu Gly Ile Thr Gln Ser Leu
            245                 250                 255

Leu Leu Lys Asn Gln Glu Lys Ile Ala Ala Ser Phe Asn Lys Ala Ile
            260                 265                 270

Gly His Met Gln Glu Gly Phe Arg Ser Thr Ser Leu Ala Leu Gln Gln
            275                 280                 285

Ile Gln Asp Val Val Ser Lys Gln Ser Ala Ile Leu Thr Glu Thr Met
290                 295                 300

Ala Ser Leu Asn Lys Asn Phe Gly Ala Ile Ser Ser Val Ile Gln Glu
305                 310                 315                 320

Ile Tyr Gln Gln Phe Asp Ala Ile Gln Ala Asn Ala Gln Val Asp Arg
                325                 330                 335

Leu Ile Thr Gly Arg Leu Ser Ser Leu Ser Val Leu Ala Ser Ala Lys
            340                 345                 350

Gln Ala Glu Tyr Ile Arg Val Ser Gln Gln Arg Glu Leu Ala Thr Gln
            355                 360                 365

Lys Ile Asn Glu Cys Val Lys Ser Gln Ser Ile Arg Tyr Ser Phe Cys
370                 375                 380

Gly Asn Gly Arg His Val Leu Thr Ile Pro Gln Asn Ala Pro Asn Gly
385                 390                 395                 400

Ile Val Phe Ile His Phe Ser Tyr Thr Pro Asp Ser Phe Val Asn Val
                405                 410                 415

Thr Ala Ile Val Gly Phe Cys Val Lys Pro Ala Asn Ala Ser Gln Tyr
            420                 425                 430

Ala Ile Val Pro Ala Asn Gly Arg Gly Ile Phe Ile Gln Val Asn Gly

```
                435                 440                 445
Ser Tyr Tyr Ile Thr Ala Arg Asp Met Tyr Met Pro Arg Ala Ile Thr
450                 455                 460

Ala Gly Asp Val Val Thr Leu Thr Ser Cys Gln Ala Asn Tyr Val Ser
465                 470                 475                 480

Val Asn Lys Thr Val Ile Thr Thr Phe Val Asp Asn Asp Asp Phe Asp
                485                 490                 495

Phe Asn Asp Glu Leu Ser Lys Trp Trp Asn Asp Thr Lys His Glu Leu
            500                 505                 510

Pro Asp Phe Asp Lys Phe Asn Tyr Thr Val Pro Ile Leu Asp Ile Asp
            515                 520                 525

Ser Glu Ile Asp Arg Ile Gln Gly Val Ile Gln Gly Leu Asn Asp Ser
530                 535                 540

Leu Ile Asp Leu Glu Lys Leu Ser Ile Leu Lys Thr Tyr Ile Lys Trp
545                 550                 555                 560

Pro Trp Tyr Val Trp Leu Ala Ile Ala Phe Ala Thr Ile Ile Phe Ile
                565                 570                 575

Leu Ile Leu Gly Trp Val Phe Phe Met Thr Gly Cys Cys Gly Cys Cys
            580                 585                 590

Cys Gly Cys Phe Gly Ile Met Pro Leu Met Ser Lys Cys Gly Lys Lys
            595                 600                 605

Ser Ser Tyr Tyr Thr Thr Phe Asp Asn Asp Val Val Thr Glu Gln Tyr
            610                 615                 620

Arg Pro Lys Lys Ser Val
625                 630

<210> SEQ ID NO 12
<211> LENGTH: 621
<212> TYPE: PRT
<213> ORGANISM: Infectious bronchitis virus (IBV)

<400> SEQUENCE: 12

Arg Arg Phe Arg Arg Ser Ile Thr Glu Asn Val Ala Asn Cys Pro Tyr
1               5                   10                  15

Val Ser Tyr Gly Lys Phe Cys Ile Lys Pro Asp Gly Ser Ile Ala Thr
            20                  25                  30

Ile Val Pro Lys Gln Leu Glu Gln Phe Val Ala Pro Leu Leu Asn Val
        35                  40                  45

Thr Glu Asn Val Leu Ile Pro Asn Ser Phe Asn Leu Thr Val Thr Asp
50                  55                  60

Glu Tyr Ile Gln Thr Arg Met Asp Lys Val Gln Ile Asn Cys Met Gln
65                  70                  75                  80

Tyr Val Cys Gly Asn Ser Leu Asp Cys Arg Asp Leu Phe Gln Gln Tyr
                85                  90                  95

Gly Pro Val Cys Asp Asn Ile Leu Ser Val Val Asn Ser Ile Gly Gln
            100                 105                 110

Lys Glu Asp Met Glu Leu Leu Asn Phe Tyr Ser Ser Thr Lys Pro Ala
        115                 120                 125

Gly Phe Asn Thr Pro Phe Leu Ser Asn Val Ser Thr Gly Glu Phe Asn
130                 135                 140

Ile Ser Leu Leu Leu Thr Thr Pro Ser Ser Pro Arg Arg Arg Ser Phe
145                 150                 155                 160

Ile Glu Asp Leu Leu Phe Thr Ser Val Glu Ser Val Gly Leu Pro Thr
                165                 170                 175
```

```
Asp Asp Ala Tyr Lys Asn Cys Thr Ala Gly Pro Leu Gly Phe Leu Lys
            180                 185                 190

Asp Leu Ala Cys Ala Arg Glu Tyr Asn Gly Leu Leu Val Leu Pro Pro
        195                 200                 205

Ile Ile Thr Ala Glu Met Gln Thr Leu Tyr Thr Ser Ser Leu Val Ala
    210                 215                 220

Ser Met Ala Phe Gly Gly Ile Thr Ala Gly Ala Ile Pro Phe Ala
225                 230                 235                 240

Thr Gln Leu Gln Ala Arg Ile Asn His Leu Gly Ile Thr Gln Ser Leu
            245                 250                 255

Leu Leu Lys Asn Gln Glu Lys Ile Ala Ala Ser Phe Asn Lys Ala Ile
        260                 265                 270

Gly Arg Met Gln Glu Gly Phe Arg Ser Thr Ser Leu Ala Leu Gln Gln
    275                 280                 285

Ile Gln Asp Val Val Asn Lys Gln Ser Ala Ile Leu Thr Glu Thr Met
290                 295                 300

Ala Ser Leu Asn Lys Asn Phe Gly Ala Ile Ser Ser Met Ile Gln Glu
305                 310                 315                 320

Ile Tyr Gln Gln Leu Asp Ala Ile Gln Ala Asn Ala Gln Val Asp Arg
            325                 330                 335

Leu Ile Thr Gly Arg Leu Ser Ser Leu Ser Val Leu Ala Ser Ala Lys
        340                 345                 350

Gln Ala Glu His Ile Arg Val Ser Gln Gln Arg Glu Leu Ala Thr Gln
    355                 360                 365

Lys Ile Asn Glu Cys Val Lys Ser Gln Ser Ile Arg Tyr Ser Phe Cys
370                 375                 380

Gly Asn Gly Arg His Val Leu Thr Ile Pro Gln Asn Ala Pro Asn Gly
385                 390                 395                 400

Ile Val Phe Ile His Phe Ser Tyr Thr Pro Asp Ser Phe Val Asn Val
            405                 410                 415

Thr Ala Ile Val Gly Phe Cys Val Lys Pro Ala Asn Ala Ser Gln Tyr
        420                 425                 430

Ala Ile Val Pro Ala Asn Gly Arg Gly Ile Phe Ile Gln Val Asn Gly
    435                 440                 445

Ser Tyr Tyr Ile Thr Ala Arg Asp Met Tyr Met Pro Arg Ala Ile Thr
450                 455                 460

Ala Gly Asp Ile Val Thr Leu Thr Ser Cys Gln Ala Asn Tyr Val Ser
465                 470                 475                 480

Val Asn Lys Thr Val Ile Thr Thr Phe Val Asp Asn Asp Asp Phe Asp
            485                 490                 495

Phe Asn Asp Glu Leu Ser Lys Trp Trp Asn Asp Thr Lys His Glu Leu
        500                 505                 510

Pro Asp Phe Asp Lys Phe Asn Tyr Thr Val Pro Ile Leu Asp Ile Asp
    515                 520                 525

Ser Glu Ile Asp Arg Ile Gln Gly Val Ile Gln Gly Leu Asn Asp Ser
530                 535                 540

Leu Ile Asp Leu Glu Lys Leu Ser Ile Leu Lys Thr Tyr Ile Lys Trp
545                 550                 555                 560

Pro Trp Tyr Val Trp Leu Ala Ile Ala Phe Ala Thr Ile Ile Phe Ile
            565                 570                 575

Leu Ile Leu Gly Trp Val Phe Phe Met Thr Gly Cys Cys Gly Cys Cys
        580                 585                 590

Cys Gly Cys Phe Gly Ile Met Pro Leu Met Ser Lys Cys Gly Lys Lys
```

595                 600                 605
Ser Ser Tyr Tyr Thr Thr Phe Asp Asn Asp Val Val Thr
    610                 615                 620

<210> SEQ ID NO 13
<211> LENGTH: 630
<212> TYPE: PRT
<213> ORGANISM: Infectious bronchitis virus (IBV)

<400> SEQUENCE: 13

Arg Arg Phe Arg Arg Ser Ile Thr Glu Ser Val Glu Asn Cys Pro Tyr
1               5                   10                  15

Val Ser Tyr Gly Lys Phe Cys Ile Lys Pro Asp Gly Ser Ile Ala Thr
            20                  25                  30

Ile Val Pro Lys Gln Leu Glu Gln Phe Val Ala Pro Leu Leu Asn Val
        35                  40                  45

Thr Glu Asn Val Leu Ile Pro Asn Ser Phe Asn Leu Thr Val Thr Asp
    50                  55                  60

Glu Tyr Ile Gln Thr Arg Met Asp Lys Val Gln Ile Asn Cys Leu Gln
65                  70                  75                  80

Tyr Ile Cys Gly Asn Ser Leu Glu Cys Arg Asn Leu Phe Gln Gln Tyr
                85                  90                  95

Gly Pro Val Cys Asp Asn Ile Leu Ser Val Val Asn Ser Val Gly Gln
            100                 105                 110

Lys Glu Asp Met Glu Leu Leu Asn Phe Tyr Ser Ser Thr Lys Pro Ala
        115                 120                 125

Gly Phe Asn Thr Pro Val Leu Ser Asn Val Ser Thr Gly Glu Phe Asn
    130                 135                 140

Ile Ser Leu Phe Leu Thr Thr Pro Ser Ser Pro Arg Arg Arg Ser Phe
145                 150                 155                 160

Ile Glu Asp Leu Leu Phe Thr Ser Val Glu Ser Val Gly Leu Pro Thr
                165                 170                 175

Asp Asp Ala Tyr Lys Asn Cys Thr Ala Gly Pro Leu Gly Phe Leu Lys
            180                 185                 190

Asp Leu Val Cys Ala Arg Glu Tyr Asn Gly Leu Leu Val Leu Pro Pro
        195                 200                 205

Ile Ile Thr Ala Glu Met Gln Thr Leu Tyr Thr Ser Ser Leu Val Ala
    210                 215                 220

Ser Met Ala Phe Gly Gly Ile Thr Ala Ala Gly Ala Ile Pro Phe Ala
225                 230                 235                 240

Thr Gln Leu Gln Ala Arg Ile Asn His Leu Gly Ile Thr Gln Ser Leu
                245                 250                 255

Leu Leu Lys Asn Gln Glu Lys Ile Ala Ala Ser Phe Asn Lys Ala Ile
            260                 265                 270

Gly His Met Gln Glu Gly Phe Arg Ser Thr Ser Leu Ala Leu Gln Gln
        275                 280                 285

Ile Gln Asp Val Val Asn Lys Gln Ser Ala Ile Leu Thr Glu Thr Met
    290                 295                 300

Ala Ser Leu Asn Lys Asn Phe Gly Ala Ile Ser Ser Val Ile Gln Glu
305                 310                 315                 320

Ile Tyr Gln Gln Leu Asp Ala Ile Gln Ala Asn Ala Gln Val Asp Arg
                325                 330                 335

Leu Ile Thr Gly Arg Leu Ser Ser Leu Ser Val Leu Ala Ser Ala Lys
            340                 345                 350

```
Gln Ala Glu Tyr Ile Arg Val Ser Gln Gln Arg Glu Leu Ala Thr Gln
            355                 360                 365

Lys Ile Asn Glu Cys Val Lys Ser Gln Ser Ile Arg Tyr Ser Phe Cys
        370                 375                 380

Gly Asn Gly Arg His Val Leu Thr Ile Pro Gln Asn Ala Pro Asn Gly
385                 390                 395                 400

Ile Val Phe Ile His Phe Ser Tyr Thr Pro Asp Ser Phe Val Asn Val
                405                 410                 415

Thr Ala Ile Val Gly Phe Cys Val Lys Pro Ala Asn Ala Ser Gln Tyr
                420                 425                 430

Ala Ile Val Pro Ala Asn Gly Arg Gly Ile Phe Ile Gln Val Asn Gly
            435                 440                 445

Ser Tyr Tyr Ile Thr Ala Arg Asp Met Tyr Met Pro Arg Ala Ile Thr
        450                 455                 460

Ala Gly Asp Ile Val Thr Leu Thr Ser Cys Gln Val Asn Tyr Val Ser
465                 470                 475                 480

Val Asn Lys Thr Val Ile Thr Thr Phe Val Asp Asn Asp Asp Phe Asp
                485                 490                 495

Phe Asn Asp Glu Leu Ser Lys Trp Trp Asn Asp Thr Lys His Glu Leu
                500                 505                 510

Pro Asp Phe Asp Lys Phe Asn Tyr Thr Val Pro Ile Leu Asp Ile Asp
            515                 520                 525

Ser Glu Ile Asp Arg Ile Gln Gly Val Ile Gln Gly Leu Asn Asp Ser
        530                 535                 540

Leu Ile Asp Leu Glu Lys Leu Ser Ile Leu Lys Thr Tyr Ile Lys Trp
545                 550                 555                 560

Pro Trp Tyr Val Trp Leu Ala Ile Ala Phe Ala Thr Ile Ile Phe Ile
                565                 570                 575

Leu Ile Leu Gly Trp Val Phe Phe Met Thr Gly Cys Cys Gly Cys Cys
                580                 585                 590

Cys Gly Cys Phe Gly Ile Met Pro Leu Met Ser Lys Cys Gly Lys Lys
            595                 600                 605

Ser Ser Tyr Tyr Thr Thr Phe Asp Asn Asp Val Val Thr Glu Gln Tyr
        610                 615                 620

Arg Pro Lys Lys Ser Val
625                 630

<210> SEQ ID NO 14
<211> LENGTH: 630
<212> TYPE: PRT
<213> ORGANISM: Infectious bronchitis virus (IBV)

<400> SEQUENCE: 14

His Arg Arg Arg Arg Ser Ile Gly Gln Asn Val Thr Ser Cys Pro Tyr
1               5                   10                  15

Val Ser Tyr Gly Arg Phe Cys Ile Glu Pro Asp Gly Ser Leu Lys Met
                20                  25                  30

Ile Val Pro Glu Glu Leu Lys Gln Phe Val Ala Pro Leu Leu Asn Ile
            35                  40                  45

Thr Glu Ser Val Leu Ile Pro Asn Ser Phe Asn Leu Thr Val Thr Asp
        50                  55                  60

Glu Tyr Ile Gln Thr Arg Met Asp Lys Val Gln Ile Asn Cys Leu Gln
65                  70                  75                  80

Tyr Val Cys Gly Asn Ser Leu Glu Cys Arg Lys Leu Phe Gln Gln Tyr
                85                  90                  95
```

-continued

```
Gly Pro Val Cys Asp Asn Ile Leu Ser Val Val Asn Ser Val Ser Gln
            100                 105                 110

Lys Glu Asp Met Glu Leu Leu Ser Phe Tyr Ser Ser Thr Lys Pro Lys
            115                 120                 125

Gly Tyr Asp Thr Pro Val Leu Ser Asn Val Ser Thr Gly Glu Phe Asn
            130                 135                 140

Ile Ser Leu Leu Leu Lys Pro Pro Ser Pro Ser Gly Arg Ser Phe
145                 150                 155                 160

Ile Glu Asp Leu Leu Phe Thr Ser Val Glu Thr Val Gly Leu Pro Thr
                165                 170                 175

Asp Ala Glu Tyr Lys Lys Cys Thr Ala Gly Pro Leu Gly Thr Leu Lys
            180                 185                 190

Asp Leu Ile Cys Ala Arg Glu Tyr Asn Gly Leu Leu Val Leu Pro Pro
            195                 200                 205

Ile Ile Thr Ala Asp Met Gln Thr Met Tyr Thr Ala Ser Leu Val Gly
            210                 215                 220

Ala Met Ala Phe Gly Gly Ile Thr Ser Ala Ala Ile Pro Phe Ala
225                 230                 235                 240

Thr Gln Ile Gln Ala Arg Ile Asn His Leu Gly Ile Thr Gln Ser Leu
            245                 250                 255

Leu Met Lys Asn Gln Glu Lys Ile Ala Ala Ser Phe Asn Lys Ala Ile
            260                 265                 270

Gly His Met Gln Glu Gly Phe Arg Ser Thr Ser Leu Ala Leu Gln Gln
            275                 280                 285

Ile Gln Asp Val Val Asn Lys Gln Ser Ala Ile Leu Thr Glu Thr Met
            290                 295                 300

Asn Ser Leu Asn Lys Asn Phe Gly Ala Ile Thr Ser Val Ile Gln Asp
305                 310                 315                 320

Ile Tyr Ala Gln Leu Asp Ala Ile Gln Ala Asp Ala Gln Val Asp Arg
                325                 330                 335

Leu Ile Thr Gly Arg Leu Ser Ser Leu Ser Val Leu Ala Ser Ala Lys
            340                 345                 350

Gln Ser Glu Tyr Ile Arg Val Ser Gln Gln Arg Glu Leu Ala Thr Gln
            355                 360                 365

Lys Ile Asn Glu Cys Val Lys Ser Gln Ser Asn Arg Tyr Gly Phe Cys
            370                 375                 380

Gly Ser Gly Arg His Val Leu Ser Ile Pro Gln Asn Ala Pro Asn Gly
385                 390                 395                 400

Ile Val Phe Ile His Phe Thr Tyr Thr Pro Glu Ser Phe Val Asn Val
                405                 410                 415

Thr Ala Ile Val Gly Phe Cys Val Asn Pro Ala Asn Ala Ser Gln Tyr
            420                 425                 430

Ala Ile Val Pro Ala Asn Gly Arg Gly Ile Phe Ile Gln Val Asn Gly
            435                 440                 445

Thr Tyr Tyr Ile Thr Ala Arg Asp Met Tyr Met Pro Arg Asp Ile Thr
            450                 455                 460

Ala Gly Asp Ile Val Thr Leu Thr Ser Cys Gln Ala Asn Tyr Val Asn
465                 470                 475                 480

Val Asn Lys Thr Val Ile Thr Thr Phe Val Glu Asp Asp Phe Asp
                485                 490                 495

Phe Asp Asp Glu Leu Ser Lys Trp Trp Asn Asp Thr Lys His Gln Leu
            500                 505                 510
```

```
-continued

Pro Asp Phe Asp Asp Phe Asn Tyr Thr Val Pro Ile Leu Asn Ile Ser
        515                 520             525

Gly Glu Ile Asp Tyr Ile Gln Gly Val Ile Gln Gly Leu Asn Asp Ser
    530             535             540

Leu Ile Asn Leu Glu Glu Leu Ser Ile Ile Lys Thr Tyr Ile Lys Trp
545             550             555                 560

Pro Trp Tyr Val Trp Leu Ala Ile Gly Phe Ala Ile Ile Ile Phe Ile
                565             570             575

Leu Ile Leu Gly Trp Val Phe Phe Met Thr Gly Cys Cys Gly Cys Cys
            580             585             590

Cys Gly Cys Phe Gly Ile Ile Pro Leu Met Ser Lys Cys Gly Lys Lys
        595             600             605

Ser Ser Tyr Tyr Thr Thr Phe Asp Asn Asp Val Val Thr Glu Gln Tyr
        610             615             620

Arg Pro Lys Lys Ser Val
625             630
```

MUTANT SPIKE PROTEIN EXTENDING THE TISSUE TROPISM OF INFECTIOUS BRONCHITIS VIRUS (IBV)

FIELD OF THE INVENTION

The present invention relates to a coronavirus spike protein (S protein). In particular an IBV S protein which, when used to produce a virus, causes the virus to have extended tissue tropism. The present invention also relates to nucleotide sequences encoding such an S protein; viral particles comprising such an S protein and their use in a vaccine to prevent and/or treat a disease.

BACKGROUND TO THE INVENTION

Infectious Bronchitis Virus (IBV)

Avian infectious bronchitis virus (IBV) is a highly infectious and contagious pathogen of domestic fowl that replicates primarily in the respiratory tract but also in epithelial cells of the gut, kidney and oviduct. IBV is a member of the Coronaviridae and genetically very similar coronaviruses cause disease in turkeys and pheasants.

Clinical signs of IB include sneezing, tracheal rales, nasal discharge and wheezing. Meat-type birds have reduced weight gain, whilst egg-laying birds lay fewer eggs. The respiratory infection predisposes chickens to secondary bacterial infections which can be fatal in chicks. The virus can also cause permanent damage to the oviduct, especially in chicks, leading to reduced egg production and quality; and kidney, sometimes leading to kidney disease which can be fatal.

Both live and attenuated vaccines are currently used in IB vaccination. To date, the most efficacious vaccines are live attenuated viruses empirically produced following blind repeated passages through embryonated eggs.

A problem with this approach is that, upon serial passaging, the immunogenicity of the virus decreases. It is necessary to achieve a balance between an acceptable degree of attenuation to make the virus safe, and an acceptable loss of immunogenicity such that the virus vaccine is still efficacious. This "balancing" of attenuation is a trial and error approach, rendering the outcome of the attenuation process uncertain.

Since attenuation by serial passage is effectively a random event, the resultant vaccine is ill-defined genetically as the molecular basis of the attenuation is to unknown. Each batch of attenuated virus will be different, making it difficult to achieve consistency of the resulting vaccine and reproducibility of the protective/therapeutic effect in vivo.

A further disadvantage is that embryonated eggs are expensive and cannot be used as a prolonged source of virus.

Growth of virus on embryonated eggs is a cumbersome process as each egg must be sterilized, candled, inoculated with virus and incubated before harvesting small volumes of allantoic fluid from each egg and pooling before purification. The lack of reliable supplies of high quality eggs results in limitations in the amount of vaccine which may be produced, particularly in an emergency situation.

In addition to these logistic and supply problems, embryonated eggs have other limitations as a host system for vaccine production. For example, there are increasing concerns about the presence of adventitious viruses, particularly retroviruses, in eggs, which would compromise the production of live, attenuated viral vaccines.

There is therefore a need for alternative IBV vaccines and methods for their production which do not suffer from the above mentioned drawbacks.

IBV is an enveloped virus that replicates in the cell cytoplasm and contains an unsegmented, single-stranded, positive sense RNA genome.

The lipid envelope contains three membrane proteins: the spike glycoprotein (S), integral membrane protein (M), and small membrane protein (E). The IBV S protein is a type I glycoprotein which oligomerizes in the endoplasmic reticulum and is assembled into virion membranes through non-covalent interactions with the membrane protein. Following incorporation into coronavirus particles, the S protein is responsible for binding to the target cell receptor and fusion of the viral and cellular membranes. The S glycoprotein consists of four domains: a signal sequence that is cleaved during synthesis; the ectodomain, which is present on the outside of the virion particle; the transmembrane region responsible for anchoring the S protein into the lipid bilayer of the virion particle; and the cytoplasmic tail.

The IBV S protein (1,162 amino acids) is cleaved into two subunits, S1 (535 amino acids; 90 kDa) comprising the N-terminal half of the S-protein, and S2 (627 amino acids; 84 kDa) comprising the C-terminal half of the S protein.

The S2 subunit associates non-covalently with the S1 subunit and contains the transmembrane and C-terminal cytoplasmic tail domains.

The present inventors have previously shown that the cell tropism of IBV, associated with growth in the mammalian cell line, Vero cells, is determined by the S2 subunit from the Beaudette strain of IBV, and that substitution of an S2 subunit with all or part of the Beaudette S2 subunit can alter (extend or reduce) the Vero cell tropism of the virus, depending on the cell tropism of the virus from which the S2 subunit was derived (WO 2011/004146).

They have shown that for an IBV strain such as M41, which has restricted tissue tropism and is unable to grow on Vero cells, the substitution of the S2 subunit with all or part of the S protein from IBV Beaudette results in a virus which is capable of growing on cell lines such as Vero cells.

The extended cell tropism conferred on the virus by the substitution of all or part of their S2 subunits means that virus stock for vaccine production can be produced by growing on cell lines, rather than embryonated eggs or primary cells.

The use of cell lines such as Vero cell has many advantages:
  (i) it has been previously validated for growth of viruses and diagnostic purposes;
  (ii) the cells (and therefore virus) can be grown in suspension, rather than flat beds; and
  (iii) it is possible to achieve consistent yields.

The present inventors previously identified a "motif" in the IBV strain Beaudette, which is able to confer the ability to grow on Vero cells.

The present inventors have now identified a number of amino acid substitutions which, when used in conjunction with the Beaudette motif, further enhances the ability of the virus to grow on cell lines.

SUMMARY OF ASPECTS OF THE INVENTION

Thus, in a first aspect, the present invention provides an infectious bronchitis virus (IBV) spike protein (S protein) which is based on an S protein from an IBV strain with restricted tissue tropism, but which comprises the sequence XBBXBX (SEQ ID NO: 3) in the part of the S2 protein corresponding to residues 686 to 691 of the sequence given as SEQ ID NO: 2, where B is a basic residue and X is any amino acid; and which comprises at least one of the following amino acid substitutions with reference to the position numbering of SEQ ID NO: 2:

Leucine (L) to Phenylalanine (F) at position 578
Asparagine (N) to Serine (S) at position 617
Asparagine (N) to Serine (S) at position 826
Leucine (L) to Phenylalanine (F) at position 857 and
Isoleucine (I) to Valine (V) at position 1000 such that an IBV virus comprising the S protein has extended tissue tropism.

The IBV S protein may comprise the sequence SRRKRS (SEQ ID NO: 4) or SRRRRS (SEQ ID NO: 5) in the part of the S2 protein corresponding to between residues 686 and 691 of the sequence given as SEQ ID No. 2.

The IBV S protein may comprise the sequence SRRKRSLIE (SEQ ID NO: 6) or SRRRRSVIE (SEQ ID NO: 7) in the part of the S2 protein corresponding to between residues 686 and 694 of the sequence given as SEQ ID No. 2.

The IBV S protein may comprise the following amino acid substitutions with reference to the position numbering of SEQ ID NO:2:

Leucine (L) to Phenylalanine (F) position 578 and
Asparagine (N) to Serine (S) position 617.

The IBV S protein may comprise the following amino acid substitutions with reference to the position numbering of SEQ ID NO:2:

Asparagine (N) to Serine (S) position 826
Leucine (L) to Phenylalanine (F) position 857 and
Isoleucine (I) to Valine (V) position 1000.

In a second aspect, the present invention provides a nucleotide sequence capable of encoding an S protein according to the first aspect of the invention.

The invention also provides plasmid comprising a nucleotide sequence according to the second aspect of the invention.

In a third aspect, the present invention provides a viral particle comprising an S protein according to the first aspect of the invention, and/or a nucleotide sequence according to the second aspect of the invention.

The viral particle may be a recombinant vaccinia virus (rVV) or a coronavirus.

The viral particle may be capable of growing on a cell line such as Vero cells.

The infection of Vero cells by a viral particle according to the third aspect of the invention may be blocked by soluble heparin.

In a fourth aspect, the present invention provides a cell capable of producing a viral particle according to the third aspect of the invention. The cell may, for example, be a cell, such as a primary chick kidney cell, capable of producing recombinant virus using a reverse genetics system, or a cell infected with a viral particle according to the third aspect of the invention.

The cell infected with a viral particle according to the third aspect of the invention may be derivable from a cell line, such as a Vero cell.

In a fifth aspect, the present invention provides a vaccine comprising a viral particle of the fourth aspect of the invention.

Further aspects of the invention provide:

(i) a method for treating and/or preventing a disease in a subject which comprises the step of administering a vaccine according to the fifth aspect of the invention to the subject;

(ii) a vaccine according to the fifth aspect of the invention for treating and/or preventing a disease in a subject;

(iii) the use of a viral particle according to the third aspect of the invention in the manufacture of a vaccine for treating and/or preventing a disease in a subject;

(iv) a method for producing a vaccine according to the fifth aspect of the invention, which comprises the step of infecting Vero cells with a viral particle according to the third aspect of the invention; and (vi) a cell culture comprising a cell or a population of cells according to the fourth aspect of the invention.

DESCRIPTION OF THE FIGURES

FIG. 1 Growth kinetics of the six variant rIBVs on Vero cells all the rIBVs investigated had been passaged 7 times on Vero cells.

FIG. 2 Growth kinetics of the six variant rIBVs on Vero cells without previous passage on Vero cells.

FIG. 3 Alignment of amino acid sequences of complete S proteins for IBV Beaudette (SEQ ID NO: 1), M41 (SEQ ID NO: 2), H120 (SEQ ID NO: 9), and QX (SEQ ID NO: 10). The S1/S2 junction is at position 537. The amino acid positions in the S2 subunit are 2 higher than shown in SEQ ID No. 1 (578 becomes 580) due to the QX S1 sequence being two amino acids longer than the other S1 sequences.

FIG. 4 Alignment of amino acid sequences of the S2 subunits, for IBV Beaudette (SEQ ID NO: 11), M41 (SEQ ID NO: 12), H120 (SEQ ID NO: 13), and QX (SEQ ID NO: 14). The amino acid modifications tested in the six rIBVs described in the Examples are marked with an arrow.

DETAILED DESCRIPTION

IBV

Avian infectious bronchitis (IB) is an acute and highly contagious respiratory disease of chickens which causes significant economic losses. The disease is characterized by respiratory signs including gasping, coughing, sneezing, tracheal rales, and nasal discharge. In young chickens, severe respiratory distress may occur. In layers, respiratory distress, nephritis, decrease in egg production, and loss of internal egg quality and egg shell quality are common.

In broilers, coughing and rattling are common clinical signs, rapidly spreading in all the birds of the premises. Morbidity is 100% in non-vaccinated flocks. Mortality varies depending on age, virus strain, and secondary infections but may be up to 60% in non-vaccinated flocks.

The first IBV serotype to be identified was Massachusetts, but in the United States several serotypes, including Arkansas and Delaware, are currently circulating, in addition to the originally identified Massachusetts type.

The IBV strain Beaudette was derived following at least 150 passages in chick embryos. IBV Beaudette is no longer pathogenic for adult birds but rapidly kills embryos.

H120 is a commercial live IBV Massachusetts serotype vaccine strain, attenuated by approximately 120 passages in embryonated chicken eggs. H52 is another Massachusetts strain, and represents an earlier and slightly more pathogenic passage virus (passage 52) during the development of H120. Vaccines based on H120 and H52 are commonly used.

IB QX is a virulent field isolate of IBV. It is sometimes known as "Chinese QX" as it was originally isolated following outbreaks of disease in the Qingdao region in China. Since that time the virus has crept towards Europe. From 2004, severe egg production issues have been identified with a very similar virus in parts of Western Europe, predominantly in the Netherlands, but also reported from Germany, France, Belgium, Denmark and in the UK.

The virus isolated from the Dutch cases was identified by the Dutch Research Institute at Deventer as a new strain that they called D388. The Chinese connection came from further tests which showed that the virus was 99% similar to the Chinese QX viruses. An attenuated live QX-like infectious bronchitis virus strain has now been developed.

S Protein

The IBV S protein comprises a large, heavily glycosylated ectodomain that can be cleaved during biosynthesis into two subunits (S1 and S2) by a furin-like enzyme in the Golgi apparatus. S1 comprises the receptor binding domain and S2 comprises the fusion domain. The S protein of IBV is fully cleaved at the S1/S2 boundary, to especially in chicken embryo systems.

The S2 domain contains five domains or functional regions: two domains, HR1 and HR2 form helical structures resulting in the stalk structure of the protein; a transmembrane domain responsible for anchoring the protein to the virion membrane; a cysteine-rich cytoplasmic domain responsible for interacting with other virus structural proteins and a fifth domain, the fusion peptide, responsible for virus-cell fusion or cell-to-cell fusion.

The amino acid sequences for IBV strains Beaudette and M41 are as follows:

SEQ ID No. 1: IBV Beaudette S protein. The full Beaudette-specific motif is shown in bold (amino acids 686-694).

```
   1 mlvtplllvt llcalcsavl ydsssyvyyy qsafrppsgw hlqggayavv nissefnnag
  61 sssgctvgii hggrvvnass iamtapssgm awsssqfcta hcnfsdttvf vthcykhggc
 121 pltgmlqqnl irvsamkngq lfynitvsva kyptfrsfqc vnnitsvyln gdlvytsnet
 181 idvtsagvyf kaggpitykv mrevkalayf vngtaqdvil cdgsprglla cqyntgnfsd
 241 gfypftnssl vkqkfivyre nsvnttctlh nfifhnetga npnpsgvgni qtyqtktaqs
 301 gyynfnfsfl ssfvykesnf mygsyhpsck frletinngl wfnslsysia ygplqggckq
 361 svfkgratcc yaysyggpsl ckgvysgeld hnfecgllvy vtksggsriq tateppvitq
 421 nnynnitlnt cvdyniygrt gqgfitnvtd saysynylad aglaildtsg sidifvvqge
 481 yglnyykvnp cedvnqqfvv sggklvgilt srnetgsqll enqfyikitn gtrrfrrsit
 541 envancpyvs ygkfcikpdg siativpkgl eqfvaplfnv tenvlipnsf nitvtdeyiq
 601 trmdkvqinc lqyvcgssld crklfqqygp vcdnilsvvn svggkedmel lnfysstkpa
 661 gfntpvisnv stgefnisll ltnpssrrkr sliedllfts vesvglptnd ayknctagpl
 721 gffkdlacar eyngllvlpp iitaemqaly tsslvasmaf ggitaagaip fatqlqarin
 781 hlgitqslll knqekiaasf nkaighmqeg frstslalqg iqdvvskqsa iltetmasln
 841 knfgaissvi qeiyqqfdai ganaqvdrli tgrlsslsvl asakqaeyir vsqqrelatq
 901 kinecvksqs irysfcgngr hvltipqnap ngivfihfsy tpdsfvnvta ivgfcvkpan
 961 asqyaivpan grgifiqvng syyitardmy mpraitagdv vtltscqany vsvnktvitt
1021 fvdnddfdfn delskwwndt khelpdfdkf nytvpildid seidriggvi qglndslidl
1081 eklsilktyi kwpwyvwlai afatiifili lgwvffmtgc cgcccgcfgi mplmskcgkk
1141 ssyyttfdnd vvteqyrpkk sv
```

SEQ ID No 2: IBV M41 S protein. The amino acids positions 686-691 and 578, 617, 826, 857 and 1000 are shown in bold.

```
   1 mlvtplllvt llcvlcsaal ydsssyvyyy qsafrppngw hlhggayavv nissesnnag
  61 sspgcivgti hggrvvnass iamtapssgm awsssqfcta hcnfsdttvfvthcykydgc
 121 pitgmlqknf lrvsamkngq lfynitvsva kyptfksfqc vnnitsvyln gdlvytsnet
 181 tdvtsagvyf kaggpitykv mrkvkalayf vngtaqdvil cdgsprglla cqyntgnfsd
 241 gfypfinssl vkqkfivyre nsvnttftlh nftfhnetga npnpsgvgni ltyqtqtaqs
 301 gyynfnfsfl ssfvykesnf mygsyhpscn frletinngl wfnslsysia ygplqggckq
 361 svfsgratcc yaysyggpsl ckgvysgeld lnfecgllvy vtksggsriq tateppvitr
 421 hnynnitlnt cvdyniygrt gqgfitnvtd saysynylad aglaildtsg sidifvvqge
```

```
 481 ygltyykvnp cedvnqqfvv sggklvgilt srnetgsqll enqfyikitn gtrrfrrsit 541 envancpyvs ygkfcikpdg siativpkql eqfvapllnv tenvlipnsf nitvtdeyiq 601 trmdkvqinc lqyvcgnsld crdlfqqygp vcdnilsvvn sigqkedmel lnfysstkpa 661 gfntpflsnv stgefnisll lttpssprrr sfiedllfts vesvglptdd ayknctagpl 721 gflkdlacar eyngllvlpp iitaemqtly tsslvasmaf ggitaagaip fatqlqarin 781 hlgitqslll knqekiaasf nkaigrmqeg frstslalgg iqdvvnkqsa iltetmasln 841 knfgaissvi qeiyqqldai ganagvdrli tgrlsslsvl asakqaehir vsggrelatq 901 kinecvksqs irysfcgngr hvltipqnap ngivfihfsy tpdsfvnvta ivgfcvkpan 961 asqyaivpan grgifiqvng syyitardmy mpraitagdi vtltscqany vsvnktvitt 1021 fvdnddfdfn delskwwndt knelpdfdkf nytvpildid seidriqgvi qglndslidl 1081 eklsilktyi kwpwyvwlai afatiifili lgwvffmtgc cgcccgcfgi mplmskcgkk 1141 ssyyttfdnd vvtegnrpkk sv
```

Figure 3:
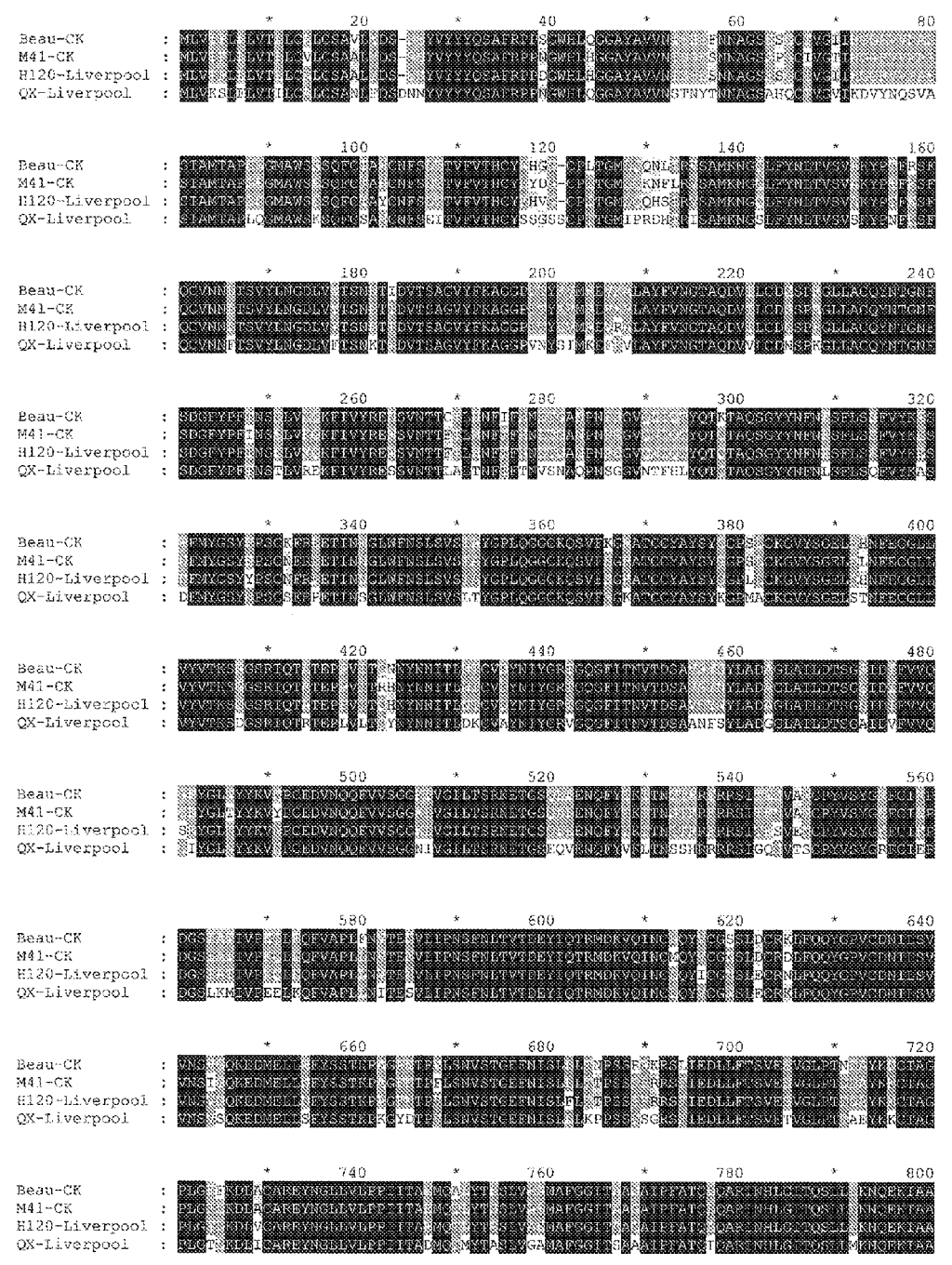
Figure 3:
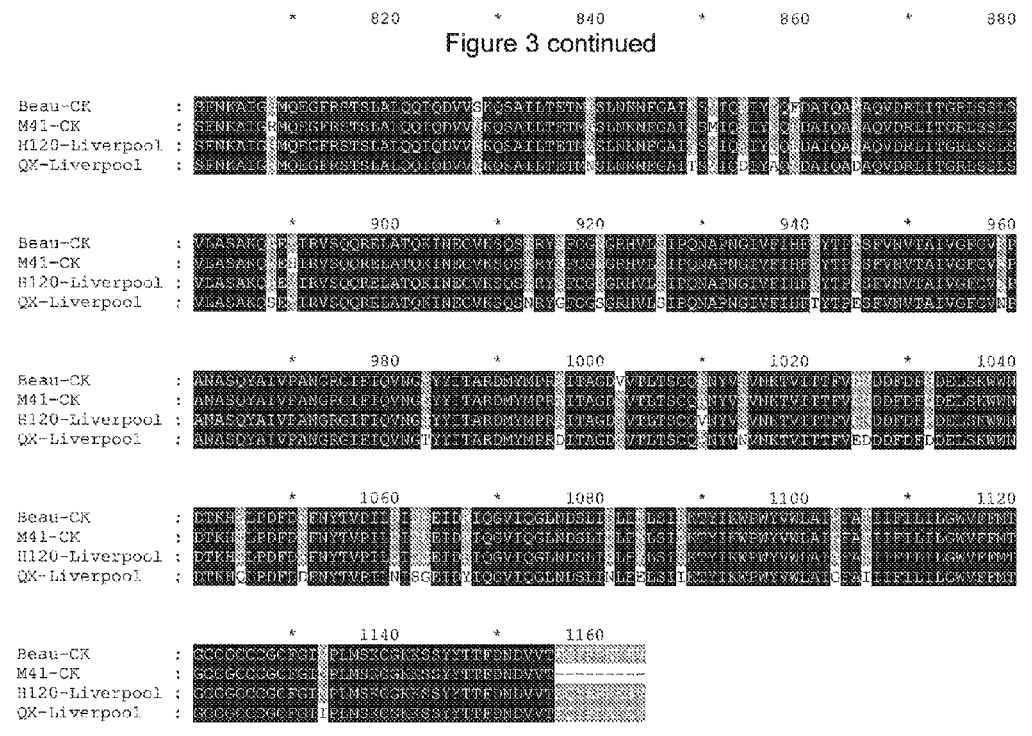

FIG. 3 shows an alignment between IBV strains Beaudette, M41, H120 and QX S proteins.

Figure 4:
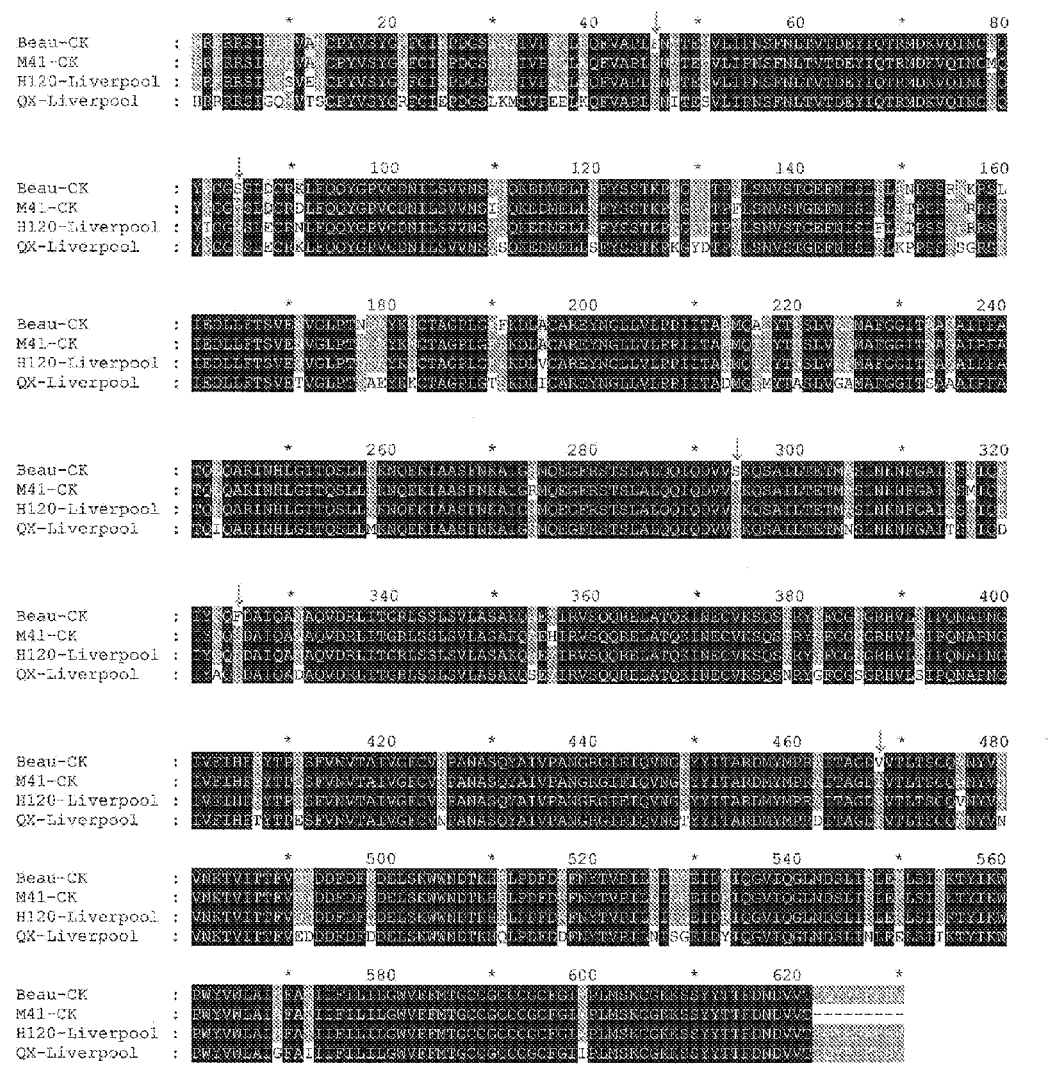

FIG. 4 shows an alignment between IBV strains Beaudette, M41, H120 and QX S2 subunits.

Tissue Tropism

Coronaviruses show strong species and tissue tropism. Likewise, clinical isolates of IBV show distinct tropism both in vivo and in cell culture.

The M41 strain has been adapted for growth on primary chick kidney (CK) cells and is restricted to infection of primary chicken cells, and so needs to be grown on embryonated eggs or CK cells.

The Beaudette strain, on the other hand, is known to be able to infect a range of cells in culture, including Vero and baby hamster kidney (BHK-21) cells.

An IBV strain with restricted tissue tropism is able to infect a smaller number of cell types than a coronavirus with extended tissue tropism.

An IBV strain with restricted tissue tropism, may, for example, be restricted to infection of primary cells, whereas an IBV strain with extended tissue tropism may (in addition to being able to infect primary cells) be able to infect one or more cell lines.

An IBV strain with extended tissue tropism may, for example, have the capacity to infect Vero cells.

The Vero cell lineage was isolated in 1962 from kidney epithelial cells extracted from an African green monkey (*Cercopithecus aethiops*). Vero cells are used for many experimental and clinical purposes, including acting as host cells for growing virus.

The Vero cell lineage is continuous in that it can be replicated through many cycles of division and not become senescent.

The Vero cell lineage has been licensed for use in the manufacture of vaccines and is currently used for the production of polio and rabies vaccines.

An IBV strain with restricted tissue tropism may be immunogenic and capable of inducing a protective or therapeutic immune response in vivo. Examples of strains with restricted tissue tropism include the strains currently used for vaccine production. For IBV, this includes strains such as: H52, H120, Ma5, 4/91, D41, D274, W93 and QX. The strain with restricted tissue tropism may be or be derived from an isolate "from the field" such as BJ1, BJ2, or BJ3 (Li and Yang (2001) Avian Pathol 30:535-541).

An example of an IBV strain with extended tissue tropism is IBV Beaudette.

Cell tropism may be established experimentally by simply challenging a given cell type with infection by a virus. The cytopathic effect (cpe) and the degree of formation of syncytia may then be analysed after a certain number of passages. Change in morphology of the infected cells may be analysed using microscopy.

Variant S Protein

The present invention relates to an infectious bronchitis virus (IBV) spike protein (S protein) which is based on an S protein from an IBV strain with restricted tissue tropism, but which comprises a "Beaudette specific motif" together with one or more Beaudette-specific amino acid substitutions, such that an IBV virus comprising the S protein has extended tissue tropism.

The term "based on" indicates that at least the S1 domain is derived or derivable from the strain with restricted tissue tropism. The majority of S2 domain may also be derived or derivable from the strain with restricted tissue tropism. For example, the transmembrane and/or cytoplasmic domains may be derived or derivable from the strain with restricted tissue tropism. The S2 domain may correspond to the sequence of the S2 domain from the strain with restricted tissue tropism, subject to the following changes:

(1) insertion of a "Beaudette-specific motif" in in the part of the S2 protein corresponding to residues 686 to 691 of the sequence given as SEQ ID No. 2;

(2) amino acid substitution in one or more of the following positions, with reference to SEQ ID No. 2: 578, 617, 826, 857, 1000.

The S2 domain may comprise some additional amino acid mutations, such as substitutions, insertions or deletions, as long as they do not significantly affect the capacity of the S2 subunit to extend the tissue tropism of the resultant virus. The additional amino acid mutations may, for example, arise as a result of passage on a cell line such as Vero cells. The S2 domain may, for example comprise an additional mutation at amino acid position 865 (glutamine (Q) to histidine (H)).

Considering the entire S2 sequence without amino acid positions 686-694, 578, 617, 826, 857 and 1000, substantially all of the remainder of the sequence may correspond to that of the wild-type S2 sequence from the strain with restricted tissue tropism.

The term "substantially all" means that the S2 protein has at least 90, 95 or 98% of the wild-type sequence as a whole but ignoring amino acid positions 686-694, 578, 617, 826, 857 and 1000.

The term "wild type" is used to mean a polypeptide having a primary amino acid sequence which is identical with the native protein (i.e., the viral protein).

Identity comparisons can be conducted by eye, or more usually, with the aid of readily available sequence comparison programs. These commercially available computer programs can calculate % identity between two or more sequences. A suitable computer program for carrying out such an alignment is the GCG Wisconsin Bestfit package (University of Wisconsin, U.S.A.; Devereux et al., 1984, Nucleic Acids Research 12:387). Examples of other software that can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However, for some applications, it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1): 187-8 and tati ana@ncbi.nlm.nih.gov).

The sequence may have one or more deletions, insertions or substitutions of amino acid residues which produce a silent change and result in a functionally equivalent molecule. Deliberate amino acid substitutions may be made on the basis of similarity in polarity, charge, solubility, hydrophobicity, hydrophilicity, and/or the amphipathic nature of the residues as long as the activity is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

An alignment between S proteins of different strains is straightforward because coronaviruses share a common domain structure and, between strains, should have a relatively high level of sequence identity. Alignment software may be used such as the BLAST™ package described above.

Amino Acid Positioning

The S protein of the present invention comprises the sequence XBBXBX (SEQ ID NO: 3) in the part of the S2 protein corresponding to residues 686 to 691 of the sequence given as SEQ ID NO: 2, where B is a basic residue and X is any amino acid; and comprises at least one of the following amino acid substitutions with reference to the position numbering of SEQ ID NO:2:

Leucine (L) to Phenylalanine (F) at position 578
Asparagine (N) to Serine (S) at position 617
Asparagine (N) to Serine (S) at position 826
Leucine (L) to Phenylalanine (F) at position 857 and
Isoleucine (I) to Valine (V) at position 1000.

Sequence ID NO: 2 is the sequence of IBV strain M41 S protein. It may be that the S protein from other IBV strains has slightly different amino acid numbering. For example, the S1 sequence of the QX strain is two amino acids longer than the S1 sequences of strains such as M1, Beaudette and H120. This means that for an S protein according to the invention based on QX, the XBBXBX (SEQ ID NO: 3) motif would appear in the section of sequence at position 688-693. The above mentioned mutations would be at positions 580, 619, 828, 859 and 1002.

The phrase "with reference to the position numbering of SEQ ID No. 2" indicates that the amino acid position is equivalent to the one shown for the M41 S protein sequence shown in SEQ ID No 1. It will be appreciated that the actual number of the amino acid from the N-terminus of the protein may vary between IBV S proteins of different strains, as it does for QX as explained above. However, it is should be clear from an alignment of the IBV S protein with the M41 sequence of SEQ ID No. 1 which is the "equivalent" amino acid position.

An alignment of S proteins from various IBV strains is shown in FIG. 3.

The position of the motif and mutations can also be given in the context of the S2 subunit.

An alignment of the S2 subunits from various IBV strains is shown in FIG. 4. The corresponding amino acid positions for the S2 subunit is shown in the following Table:

| | M41 S protein position | M41 S2 subunit position |
|---|---|---|
| XBBXBX (SEQ ID NO: 3) motif | 686-691 | 154-159 |
| L→F | 578 | 46 |
| N→S | 617 | 85 |
| N→S | 826 | 294 |
| L→F | 857 | 325 |
| I→V | 1000 | 468 |

Thus the S protein of the present invention comprises the sequence XBBXBX (SEQ ID NO: 3) in the part of the S2 protein corresponding to residues 154 to 159 of the sequence shown in FIG. 4, where B is a basic residue and X is any amino acid; and comprises at least one of the following amino acid substitutions with reference to the position numbering of the sequences shown in FIG. 4:

Leucine (L) to Phenylalanine (F) at position 46
Asparagine (N) to Serine (S) at position 85
Asparagine (N) to Serine (S) at position 294
Leucine (L) to Phenylalanine (F) at position 325 and
Isoleucine (I) to Valine (V) at position 468.

Nucleotide Sequence

The present invention also provides a nucleotide sequence capable of encoding the S protein of the present invention.

The nucleotide sequence may be natural, synthetic or recombinant. It may be double or single stranded, it may be DNA or RNA or combinations thereof. It may, for example, be cDNA, a PCR product, genomic sequence or mRNA.

The nucleotide sequence may be codon optimised for production in the host/host cell of choice.

It may be isolated, or as part of a plasmid, virus or host cell.

Plasmid

A plasmid is an extra-chromosomal DNA molecule separate from the chromosomal DNA which is capable of replicating independently of the chromosomal DNA. They are usually circular and double-stranded.

Plasmids, or vectors (as they are sometimes known), may be used to express a protein in a host cell. For example a bacterial host cell may be transfected with a plasmid capable of encoding a particular protein, in order to express that protein. The term also includes yeast artificial chromosomes and bacterial artificial chromosomes which are capable of accommodating longer portions of DNA.

The plasmid of the present invention comprises a nucleotide sequence capable of encoding the S gene. It may also comprise one or more additional coronavirus nucleotide sequence(s), or nucleotide sequence(s) capable of encoding one or more other coronavirus proteins such as the replicase gene and/or gene 3.

The plasmid may also comprise a resistance marker, such as the guanine xanthine phosphoribosyltransferase gene (gpt) from *Escherichia coli*, which confers resistance to mycophenolic acid (MPA) in the presence of xanthine and hypoxanthine and is controlled by the vaccinia virus $P_{7.5}$ early/late promoter.

Viral Particle

The present invention also relates to a viral particle with an S gene of the present invention. The viral particle may, for example, be a recombinant vaccinia virus (rVV) or a coronavirus.

The viral particle may be recombinant.

The viral particle may be made using a reverse genetics system, such as a vaccinia-virus based reverse genetics system.

Suitable reverse genetics systems are known in the art (Casais et al (2001) J. Virol 75:12359-12369; Casais et al (2003) J. Virol. 77:9084-9089; Britton et al (2005) J. Virological Methods 123:203-211; Armesto et al (2008) Methods in Molecular Biology 454:255-273).

Cell

The viral particle may be used to infect a cell.

Since the viral particle comprising the S gene of the present invention has extended tissue tropism, the cell may be derivable from or a part of a cell line.

The cell may, for example, be a baby hamster kidney cell (e.g. BHK-21) or a Vero cell.

The cell may be used to produce the viral particle.

Thus the present invention also provides a method for producing a viral particle which comprises the following steps:

(i) infection of a cell with a viral particle according to the sixth aspect of the invention;
(ii) allowing the virus to replicate in the cell; and
(iii) harvesting the progeny virus.

The cell may be from or part of a cell line, such as a Vero cell. Viral particles may be harvested, for example from the supernatant by methods known in the art, and optionally purified.

The present invention also provides a cell capable of producing a recombinant viral particle according to the fourth aspect of the invention using a reverse genetics system. For example, the cell may comprise a recombining virus genome comprising a nucleotide sequence capable of encoding the S gene of the present invention.

The cell may be able to produce recombinant recombining virus (e.g. vaccinia virus) containing the S gene. The cell may be a Vero cell.

Alternatively the cell may be capable of producing recombinant coronavirus by a reverse genetics system. The cell may express or be induced to express T7 polymerase in order to rescue the recombinant viral particle. The cell may be a CK cell.

Vaccine

The viral particle may be used to produce a vaccine.

The vaccine may by a live attenuated form of the viral particle.

The present invention also relates to a method for producing such a vaccine which comprises the step of infecting cells, for example Vero cells, with a viral particle comprising a chimaeric protein according to the first aspect of the invention.

Vaccination Method

The viral particle of the present invention may be used to treat and/or prevent a disease.

To "treat" means to administer the vaccine to a subject having an existing disease in order to lessen, reduce or improve at least one symptom associated with the disease and/or to slow down, reduce or block the progression of the disease.

To "prevent" means to administer the vaccine to a subject who has not yet contracted the disease and/or who is not showing any symptoms of the disease to prevent or impair the cause of the disease (e.g. infection) or to reduce or prevent development of at least one symptom associated with the disease.

The disease may be caused by infections bronchitis virus.

The disease may be infectious bronchitis (IB).

The vaccine may be administered to hatched chicks or chickens, for example by eye drop or intranasal administration. Although accurate, these methods can be expensive e.g. for large broiler flocks. Alternatives include spray inoculation of administration to drinking water but it can be difficult to ensure uniform vaccine application using such methods.

The vaccine may be provided in a form suitable for its administration, such as an eye-dropper for intra-ocular use.

The vaccine may be administered by the in ovo inoculation, for example by injection of embryonated eggs. In ovo vaccination has the advantage that is provides an early stage resistance to the disease. It also facilitates the administration of a uniform dose per subject, unlike spray inoculation and administration via drinking water.

The vaccine may be administered to any suitable compartment of the egg, including allantoic fluid, yolk sac, amnion, air cell or embryo. It may be administered below the shell (aircell) membrane and chorioallantoic membrane.

Usually the vaccine is injected into embryonated eggs during late stages of embryonic development, generally during the final quarter of the incubation period, such as 3-4 days prior to hatch. In chickens, the vaccine may be administered between day 15-19 of the 21-day incubation period, for example at day 17 or 18.

The process can be automated using a robotic injection process, such as those described in WO 2004/078203.

The vaccine may be administered together with one or more other vaccines, for example, vaccines for other diseases, such as Newcastle disease virus (NDV). The present invention also provides a vaccine composition comprising a vaccine according to the invention together with one or more other vaccine(s). The present invention also provides a kit comprising a vaccine according to the invention together with one or more other vaccine(s) for separate, sequential or simultaneous administration.

The vaccine or vaccine composition of the invention may be used to treat an avian subject. For example, the subject may be a chick or chicken.

Typically, a physician or veterinarian will determine the actual dosage which will be most suitable for an individual subject or group of subjects and it will vary with the age, weight and response of the particular subject(s).

The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as (or in addition to) the carrier, excipient or diluent, any suitable binder(s), lubricant(s), suspending agent(s), coating agent(s), solubilising agent(s), and other carrier agents that may aid or increase the delivery or immunogenicity of the virus.

The invention will now be further described by way of Examples, which are meant to serve to assist one of ordinary skill in the art in carrying out the invention and are not intended in any way to limit the scope of the invention.

EXAMPLES

Example 1

Generation of Recombinant IBVs Comprising Beaudette-derived Amino Acids

The present inventors have previously shown that the Beaudette-specific motif was able to confer the ability to grow on Vero cells but not to the same extent as the complete Beaudette S2 subunit. In the present inventors' previous work, they replaced the equivalent Beaudette-specific motif sequence in the M41 S2 subunit in BeauR-M41(S) with the Beaudette-specific motif. The resultant rIBV, BeauR-M41-S-BeauR-Hep, was able to grow on Vero cells, however, kinetic studies showed that it did not grow to the same extent as the rIBV expressing an S protein comprising S1 from M41 and a complete S2 from Beaudette.

In the present study, the present inventors investigated whether other Beaudette-specific amino acids may be involved in the acquisition of the ability to grow on Vero cells.

To this end, a series of rIBVs were generated based on BeauR-M41-S-BeauR-Hep in which other Beaudette-derived amino acids were introduced. This was achieved by generating BeauR-M41-S-BeauR-Hep based cDNAs that had the Beaudette-specific amino acids, $_{578}$F, $_{617}$S, $_{826}$S, $_{857}$F and $_{1000}$I, identified in the Beaudette S2, introduced into the S glycoprotein of rIBV BeauR-M41-S-BeauR-Hep to replace the corresponding M41 amino acids $_{578}$L, $_{617}$N, $_{826}$N, $_{857}$L and $_{1000}$V.

The changes (M41 to Beaudette) were:—
Leucine (L) to Phenylalanine (F) position 578
Asparagine (N) to Serine (S) position 617
Asparagine (N) to Serine (S) position 826
Leucine (L) to Phenylalanine (F) position 857 and
Isoleucine (I) to Valine (V) position 1000

Two separate regions of the M41 S glycoprotein containing the desired amino acid changes were synthesised by Geneart and cloned into the transfer/recombination vector pGPTNEB 193. These were used to introduce the mutations into the BeauR-M41-S-BeauR-Hep full-length cDNA cloned into the vaccinia virus genome using a transient dominant selection (TDS) method for modifying the IBV genome. Recombinant vaccinia viruses were screened to identify isolates containing different combinations of the Beaudette-specific S2 amino acids. A further TDS was carried out to introduce all five Beaudette-specific amino acids into the BeauR-M41-S-BeauR-Hep full-length cDNA. Resultant recombinant vaccinia viruses were screened by sequence analysis to identify IBV cDNA sequences that contained all the Beaudette-specific amino acids.

Infectious rIBVs with different combinations of the Beaudette-specific amino acids in the S2 subunit of the BeauR-M41-S-BeauR-Hep S glycoprotein were then rescued. In order to do this, the recombinant vaccinia viruses containing the BeauR-M41-S-BeauR-Hep cDNA with the modified S2 sequences were semi-purified and the DNA was extracted. Primary CK cells were transfected with the recombinant vaccinia virus DNA to recover the infectious rIBVs, which were subsequently serially passaged three times on CK cells.

Six different rIBVs were rescued with different combinations of mutations as follows:
MSBH-NS-N to S at position 617
MSBH-LFNS-L to F at 578 and N to S at 617
MSBH-IV-I to V at 1000
MSBH-LFIV-L to F at 857 and I to V at 1000
MSBH-NSLFIV-N to S at 826, L to F at 857 and I to V at 1000
MSBH-LFNSNSLFIV-L to F at 578, N to S at 617, N to S at 826, L to F at 857 & I to V at 1000

The growth kinetics of the six rIBVs described above were analysed on CK cells and it was found that variants grew with kinetics similar to the parent virus, rIBV BeauR-M41-S-BeauR-Hep (data not shown).

The rIBVs were serially passaged seven times on Vero cells and the S genes were sequenced.

Sequence analysis showed that, after passage on Vero cells, all six rIBVs had additional amino acid changes when compared to the P3 CKC parental virus, with one amino acid at amino acid position 865 (glutamine (Q) to histidine (H)) common to three viruses. This mutation also occurs in some other viruses, so is thought not to be directly responsible for enhancing growth in Vero cells but it may interact with the other substitutions which were engineered into the M41 S2. The Q to H mutations are thought to have arisen due to growth on Vero cells.

Example 2

Analysing the Growth Kinetics of the rIBVs of Vero Cells

Figure 1:
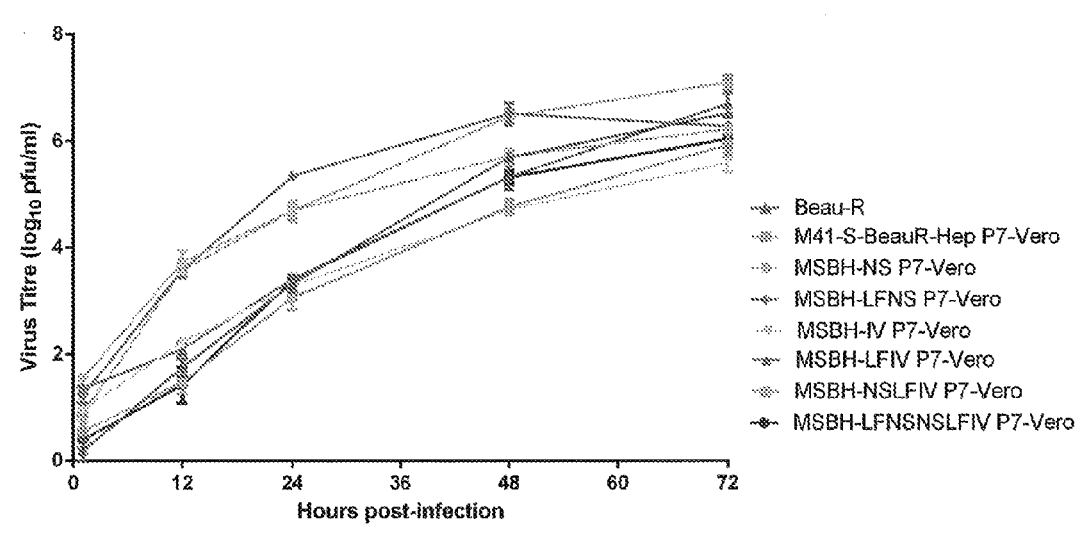

The growth characteristics of the variants on Vero cells were analysed using brightfield microscopy. Growth of the rIBV isolates were compared to rIBV BeauR-M41-S-BeauR-Hep (M41 with the Beaudette motif but no other Beaudette-derived mutations) to determine whether the five amino acids from Beaudette improve the growth kinetics. The results are shown in FIG. 1. All five Beaudette-specific S2 amino acids in the six combinations isolated in the six rIBVs improved the growth of BeauR-M41-S-BeauR-Hep on Vero cells.

The variant rIBV, MSBH-LFNSNSLFIV, that had all five Beaudette-specific amino acids introduced was found to grow the best.

These results show that other S2 Beaudette-specific amino acids in addition to the Beaudette-specific motif are involved in the ability of IBV Beaudette to grow on Vero cells. The introduction of these amino acids can be used to generate rIBVs with an S2 subunit from the parental virus but with relatively few amino acid changes.

In this experiment the rIBVs investigated had been passed 7 times on Vero cells (FIG. 1).

Figure 2:
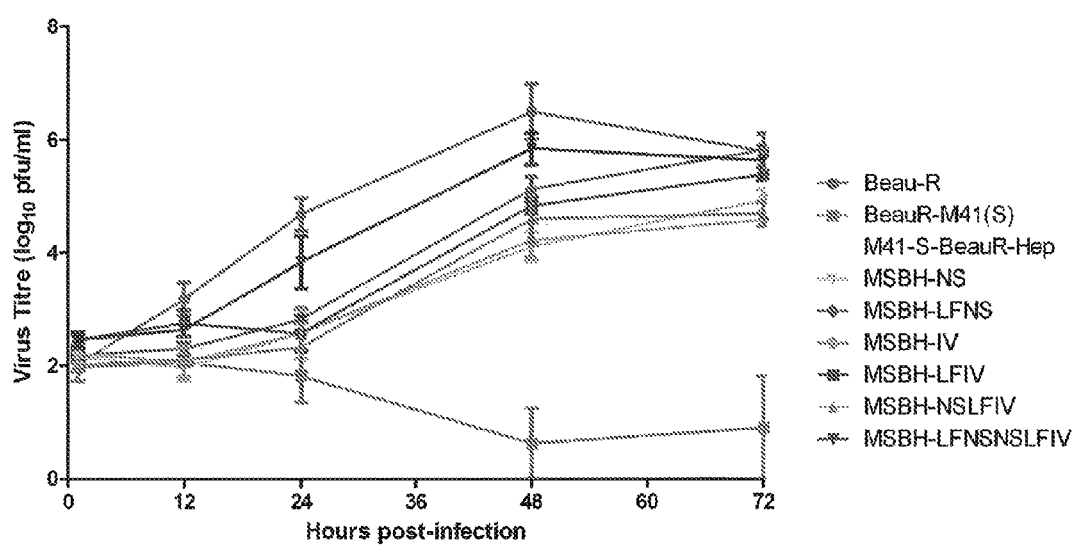

The growth kinetics was also investigated for the rIBVs in Vero cells without previous passage on Vero cells. The results are shown in FIG. 2.

BeauR-M41(S), which comprises the M41 S gene without any Beaudette S2 specific amino acids, does not grow on Vero cells. The IBV strain Beaudette was found to grow the best in this experiment. However, as shown in FIG. 1 following passage on Vero cells some of the rIBVs grow better than Beau-R. The rIBV with the Beaudette-specific motif site only, BeauR-M41-S-BeauR-Hep, does grow Vero cells, but to a lesser extent than Beaudette, even after passage on Vero cells.

However, the variant rIBVs with amino acid mutations showed improved growth after seven passages on Vero cells, most notably: MSBH-LFNS, MSBH-NSLFIV and MSBH-NS.

Interestingly, these three variants at P7-Vero (MSBH-LFNS MSBH-NSLFIV and MSBH-NS) produce a much higher titre than Beau-R at 24 hours post infection. The titre is almost 2 logs (×100 fold) better than Beau-R at 24 hours post infection. The variant sequences therefore offer an added advantage for a vaccine production as they would lead to a greatly increased yield.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, virology or related fields are intended to be within the scope of the following claims.

The invention claimed is:

1. An infectious bronchitis virus (IBV) spike protein (S protein) which comprises an S1 domain of an IBV strain with restricted tissue tropism that is unable to grow on Vero cells and an S2 domain which has at least 98% sequence identity to the S2 domain of the S protein from an IBV strain with restricted tissue tropism that is unable to grow on Vero cells, but which comprises the sequence XBBXBX (SEQ ID NO: 3) in the part of the S2 domain corresponding to residues 686 to 691 of the sequence of SEQ ID NO: 2, where B is a basic residue and X is any amino acid; and which comprises at least one of the following amino acid substitutions with reference to the position numbering of SEQ ID NO: 2:

Leucine (L) to Phenylalanine (F) at position 578;
Asparagine (N) to Serine (S) at position 617;
Asparagine (N) to Serine (S) at position 826;
Leucine (L) to Phenylalanine (F) at position; 857 and
Isoleucine (I) to Valine (V) at position 1000;
such that an IBV virus comprising the S protein is able to grow on Vero cells.

2. The IBV S protein according to claim 1, which comprises the sequence SRRKRS (SEQ ID NO: 4) or SRRRRS (SEQ ID NO: 5) in the part of the S2 domain corresponding to residues 686 and 691 of the sequence of SEQ ID NO: 2.

3. The IBV S protein according to claim 1, which comprises the sequence SRRKRSLIE (SEQ ID NO: 6) or SRRRRSVIE (SEQ ID NO: 7) in the part of the S2 domain corresponding to residues 686 and 694 of the sequence of SEQ ID NO: 2.

4. The IBV S protein according to claim 1, which comprises the amino acid substitution Asparagine (N) to Serine (S) at position 617 with reference to the position numbering of SEQ ID NO: 2.

5. The IBV S protein according to claim 1, which comprises the following amino acid substitutions with reference to the position numbering of SEQ ID NO: 2:

Leucine (L) to Phenylalanine (F) position 578 and
Asparagine (N) to Serine (S) position 617.

6. The IBV S protein according to claim 1, which comprises the following amino acid substitutions with reference to the position numbering of SEQ ID NO: 2:

Asparagine (N) to Serine (S) position 826;
Leucine (L) to Phenylalanine (F) position 857; and
Isoleucine (I) to Valine (V) position 1000.

7. A nucleic acid comprising a nucleotide sequence encoding an infectious bronchitis virus (IBV) spike protein (S protein) which comprises an S1 domain of an IBV strain with restricted tissue tropism that is unable to grow on Vero cells and an S2 domain which has at least 98% sequence identity to the S2 domain of the S protein from an IBV strain with restricted tissue tropism that is unable to grow on Vero cells, but which comprises the sequence XBBXBX (SEQ ID NO: 3) in the part of the S2 domain corresponding to residues 686 to 691 of the sequence of SEQ ID NO: 2, where B is a basic residue and X is any amino acid; and which comprises at least one of the following amino acid substitutions with reference to the position numbering of SEQ ID NO: 2:

Leucine (L) to Phenylalanine (F) at position 578;
Asparagine (N) to Serine (S) at position 617;
Asparagine (N) to Serine (S) at position 826;
Leucine (L) to Phenylalanine (F) at position 857; and
Isoleucine (I) to Valine (V) at position 1000;
such that an IBV virus comprising the S protein is able to grow on said Vero cells.

8. A plasmid comprising the nucleic acid according to claim 7.

9. A viral particle comprising an IBV S protein according to claim 1, and/or a nucleic acid comprising a nucleotide sequence encoding said IBV S protein, wherein the viral particle is capable of growing on Vero cells.

10. The viral particle according to claim 9, whose infection of Vero cells is blocked by soluble heparin.

11. A cell that comprises the nucleic acid according to claim 7 and that is capable of producing a viral particle, wherein said viral particle comprises said IBV S protein and/or a nucleotide sequence encoding said IBV S protein.

12. A Vero cell according to claim 11.

13. A vaccine comprising the viral particle according to claim 9.

14. A method for treating and/or preventing infectious bronchitis in a subject, the method comprising administering to the subject the vaccine according to claim 13.

15. A method for producing a vaccine which comprises the step of infecting Vero cells with a viral particle according to claim 9.

16. The nucleic acid according to claim 7, wherein the IBV S protein comprises the sequence SRRKRS (SEQ ID NO: 4) or SRRRRS (SEQ ID NO: 5) in the part of the S2 domain corresponding to residues 686 and 691 of the sequence of SEQ ID NO: 2.

17. The nucleic acid according to claim 7, wherein the IBV S protein comprises the sequence SRRKRSLIE (SEQ ID NO: 6) or SRRRRSVIE (SEQ ID NO: 7) in the part of the S2 domain corresponding to residues 686 and 694 of the sequence of SEQ ID NO: 2.

18. The nucleic acid according to claim 7, wherein the IBV S protein comprises the amino acid substitution Asparagine (N) to Serine (S) at position 617 with reference to the position numbering of SEQ ID NO: 2.

* * * * *